United States Patent
Perricone et al.

(10) Patent No.: US 9,645,414 B2
(45) Date of Patent: May 9, 2017

(54) LASER PROTECTION EYEWEAR

(71) Applicant: Perriquest Defense Research Enterprises, LLC, Meriden, CT (US)

(72) Inventors: Nicholas Perricone, Meriden, CT (US); Kristin Rauschenbach, Franconia, NH (US)

(73) Assignee: PerriQuest Defense Research Enterprises, LLC, Meriden, CT (US)

( * ) Notice: Subject to any disclaimer, the term of this patent is extended or adjusted under 35 U.S.C. 154(b) by 0 days.

(21) Appl. No.: 14/717,205

(22) Filed: May 20, 2015

(65) Prior Publication Data
US 2015/0338683 A1 Nov. 26, 2015

Related U.S. Application Data

(60) Provisional application No. 62/001,670, filed on May 22, 2014.

(51) Int. Cl.
| G02C 7/10 | (2006.01) |
| G02B 13/14 | (2006.01) |
| G02B 5/20 | (2006.01) |
| G02B 1/04 | (2006.01) |
| G02C 7/12 | (2006.01) |
| A61F 9/02 | (2006.01) |

(52) U.S. Cl.
CPC .............. *G02C 7/104* (2013.01); *A61F 9/022* (2013.01); *G02B 1/041* (2013.01); *G02B 5/208* (2013.01); *G02C 7/12* (2013.01); *G02C 2202/16* (2013.01)

(58) Field of Classification Search
CPC .......... G02C 7/104; G02B 5/20; G02B 5/208
USPC ............. 351/159.49, 159.59, 159.6–159.65; 359/335, 356, 359
See application file for complete search history.

(56) References Cited

U.S. PATENT DOCUMENTS

| 3,519,339 A * | 7/1970 | Hutchinson | A61F 9/022 351/159.63 |
| 5,271,872 A * | 12/1993 | Sallavanti | G02B 5/223 252/582 |
| 5,729,381 A * | 3/1998 | Havens | C03C 3/11 359/350 |

(Continued)

OTHER PUBLICATIONS

"Notification of Transmittal of the International Search Report and the Written Opinion of the International Searching Authority, or the Declaration" for PCT/US2015/061692, Mar. 4, 2016, 12 pages, International Searching Authority/KR, Korean Intellectual Property Office, Daejeon, Republic of Korea.

Dykes, Jim, Psychophysical Test of Contrast Acuity to Aid Operational Effectiveness of Aircrew Laser Eye Protection (LEP), Texas Univ at San Antonio, Fianl rept, Aug. 2005, <Retrieve: https://www.researchgate.net/publication/235176065_PsychophysicaT_Test_of_Contrast_Acuity_to_Aid_Operational_Effectiveness_of_Aircrew_Laser_Eye_Protection_LEP>.

(Continued)

*Primary Examiner* — Darryl J Collins
(74) *Attorney, Agent, or Firm* — Kurt Rauschenbach; Rauschenbach Patent Law Group, LLC

(57) ABSTRACT

A laser protection lens include an optically transparent material having a perimeter shape that follows a contour of a user's eye socket ridge, a horizontal shape, and a vertical shape. A multilayer interference coating is applied to at least one of an inside and outside surface of the optically transparent material. The multilayer interference coating has at least a 20 dB reduction of optical transmission for at least one of 445 nm, 532 nm, and 610 nm wavelengths and has at least 10 dB optical reduction over a wavelength band from at least one of 445 nm to the ultraviolet region and 610 nm the infrared region.

35 Claims, 37 Drawing Sheets

(56) References Cited

U.S. PATENT DOCUMENTS

| | | | |
|---|---|---|---|
| 6,612,697 B1* | 9/2003 | Aurelius | G02B 5/226 |
| | | | 351/159.62 |
| 7,008,056 B2 | 3/2006 | Hartley et al. | |
| 7,202,852 B2 | 4/2007 | Harvie | |
| 8,023,195 B2 | 9/2011 | Alekseyev-Popov et al. | |
| 2005/0024583 A1 | 2/2005 | Neuberger | |
| 2008/0257362 A1* | 10/2008 | Davison | A61F 9/02 |
| | | | 128/858 |
| 2009/0290119 A1* | 11/2009 | Bartholomew | G02C 1/00 |
| | | | 351/114 |
| 2010/0110370 A1 | 5/2010 | Krieg-Kowald et al. | |
| 2013/0278893 A1* | 10/2013 | Lemay | A61F 9/022 |
| | | | 351/159.57 |

OTHER PUBLICATIONS

"Notification of Transmittal of the International Search Report and the Written Opinion of The International Searching Authority, or the Declaration" for PCT/US15/031694, Sep. 1, 2015, 13 pages, International Searching Authority/KR, Korean Intellectual Property Office, Daejeon Metropolitan City, Republic of Korea.

"Notification Concerning Transmittal of International Preliminary Report on Patentability (Chapter I of the Patent Cooperation Treaty" for International Patent Application No. PCT/US2015/031694, Dec. 1, 2016, 10 Pages, The International Bureau of WIPO, Geneva, Switzerland.

* cited by examiner

Table 1

| Layer Number | Physical Thickness (nm) | Refractive Index | Layer Type |
|---|---|---|---|
| 1 | 59.4 | 2.30 | H |
| 2 | 85.8 | 1.45 | L |
| 3 | 24.2 | 2.30 | H |
| 4 | 50.7 | 1.45 | L |
| 5 | 41.1 | 2.30 | H |
| 6 | 43.6 | 1.45 | L |
| 7 | 278.3 | 2.30 | H |
| 8 | 243.4 | 1.45 | L |
| 9 | 76.3 | 2.30 | H |
| 10 | 149.7 | 1.45 | L |
| 11 | 59.4 | 2.30 | H |
| 12 | 90.7 | 1.45 | L |
| 13 | 125.0 | 2.30 | H |
| 14 | 89.4 | 1.45 | L |
| 15 | 56.71 | 2.30 | H |
| 16 | 77.5 | 1.45 | L |
| 17 | 54.0 | 2.30 | H |
| 18 | 81.1 | 1.45 | L |
| 19 | 49.0 | 2.30 | H |
| 20 | 74.3 | 1.45 | L |
| 21 | 38.2 | 2.30 | H |
| 22 | 46.6 | 1.45 | L |
| 23 | 42.6 | 2.30 | H |
| 24 | 81.5 | 1.45 | L |
| 25 | 135.1 | 2.30 | H |
| 26 | 75.0 | 1.45 | L |
| 27 | 48.4 | 2.30 | H |
| 28 | 83.0 | 1.45 | L |
| 29 | 91.4 | 2.30 | H |
| 30 | 146.5 | 1.45 | L |
| 31 | 54.2 | 2.30 | H |
| 32 | 76.8 | 1.45 | L |
| 33 | 32.3 | 2.30 | H |
| 34 | 47.5 | 1.45 | L |
| 35 | 47.5 | 2.30 | H |
| 36 | 88.1 | 1.45 | L |
| 37 | 86.5 | 2.30 | H |
| 38 | 111.8 | 1.45 | L |
| 39 | 87.3 | 2.30 | H |
| 40 | 95.3 | 1.45 | L |
| 41 | 145.8 | 2.30 | H |
| 42 | 73.1 | 1.45 | L |
| 43 | 27.5 | 2.30 | H |
| 44 | 66.4 | 1.45 | L |
| 45 | 154.1 | 2.30 | H |
| 46 | 20.9 | 1.45 | L |
| 47 | 60.1 | 2.30 | H |

FIG. 5

Table 2

| Layer Number | Physical Thickness (nm) | Refractive Index | Layer Type |
|---|---|---|---|
| 1 | 173.4 | 2.30 | H |
| 2 | 275.0 | 1.45 | L |
| 3 | 173.4 | 2.30 | H |
| 4 | 275.0 | 1.45 | L |
| 5 | 173.4 | 2.30 | H |
| 6 | 275.0 | 1.45 | L |
| 7 | 173.4 | 2.30 | H |
| 8 | 275.0 | 1.45 | L |
| 9 | 173.4 | 2.30 | H |
| 10 | 275.0 | 1.45 | L |
| 11 | 173.4 | 2.30 | H |
| 12 | 275.0 | 1.45 | L |
| 13 | 173.4 | 2.30 | H |
| 14 | 275.0 | 1.45 | L |
| 15 | 173.4 | 2.30 | H |
| 16 | 275.0 | 1.45 | L |
| 17 | 173.4 | 2.30 | H |
| 18 | 275.0 | 1.45 | L |
| 19 | 173.4 | 2.30 | H |

FIG. 7

Table 3

| Layer Number | Physical Thickness (nm) | Refractive Index | Layer Type |
|---|---|---|---|
| 1 | 93.78 | 1.45 | L |
| 2 | 37.92 | 2.30 | H |
| 3 | 11.85 | 1.45 | L |
| 4 | 62.78 | 2.30 | H |
| 5 | 97.61 | 1.45 | L |
| 6 | 28.18 | 2.30 | H |
| 7 | 204.77 | 1.45 | L |
| 8 | 56.80 | 2.30 | H |
| 9 | 89.73 | 1.45 | L |
| 10 | 113.77 | 2.30 | H |
| 11 | 89.96 | 1.45 | L |
| 12 | 56.79 | 2.30 | H |
| 13 | 204.64 | 1.45 | L |
| 14 | 29.88 | 2.30 | H |
| 15 | 94.40 | 1.45 | L |
| 16 | 57.55 | 2.30 | H |
| 17 | 62.78 | 1.45 | L |
| 18 | 9.80 | 2.30 | H |
| 19 | 92.82 | 1.45 | L |
| 20 | 56.90 | 2.30 | H |
| 21 | 89.79 | 1.45 | L |
| 22 | 102.85 | 2.30 | H |
| 23 | 121.09 | 1.45 | L |
| 24 | 55.87 | 2.30 | H |
| 25 | 191.81 | 1.45 | L |
| 26 | 5.24 | 2.30 | H |
| 27 | 155.80 | 1.45 | L |
| 28 | 56.84 | 2.30 | H |
| 29 | 132.08 | 1.45 | L |
| 30 | 96.57 | 2.30 | H |
| 31 | 90.33 | 1.45 | L |
| 32 | 57.80 | 2.30 | H |
| 33 | 175.83 | 1.45 | L |
| 34 | 57.44 | 2.30 | H |
| 35 | 90.81 | 1.45 | L |
| 36 | 112.36 | 2.30 | H |

FIG. 9

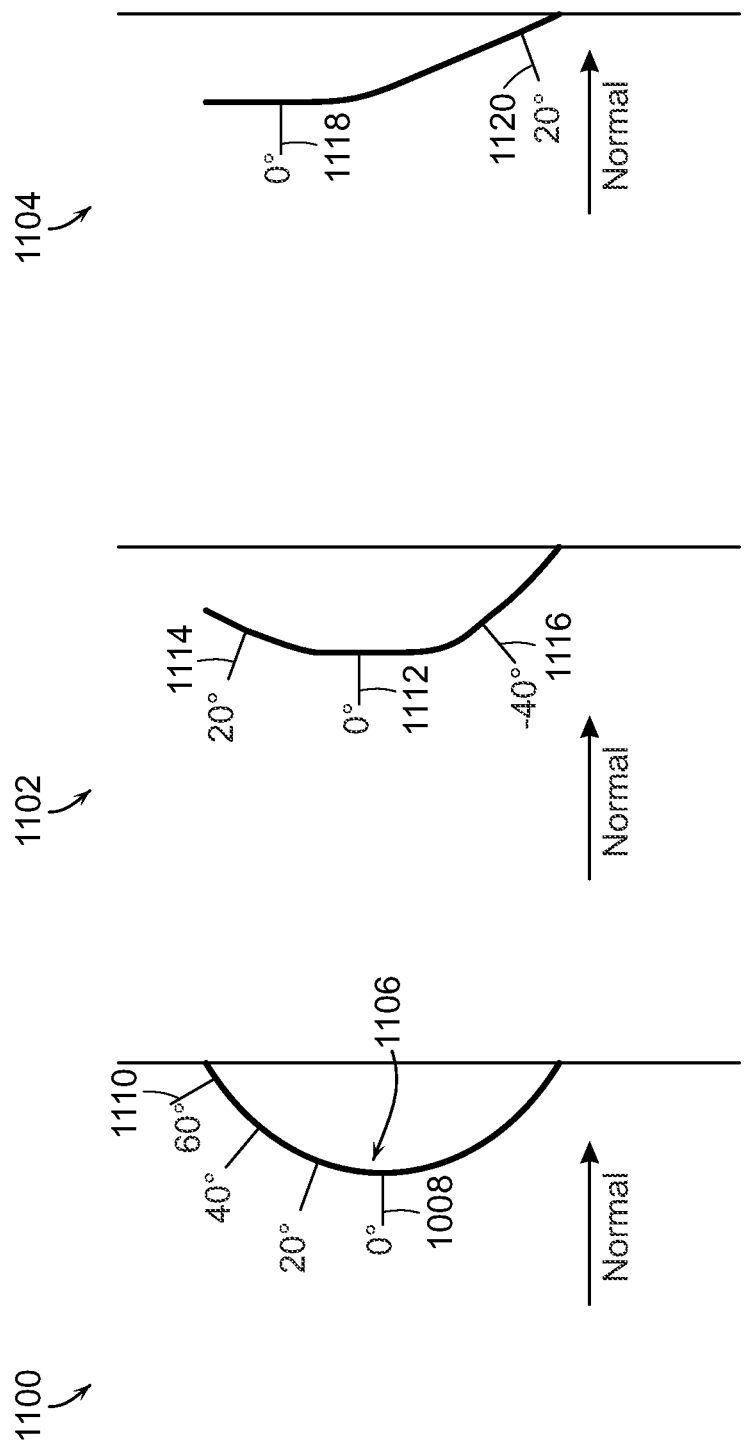

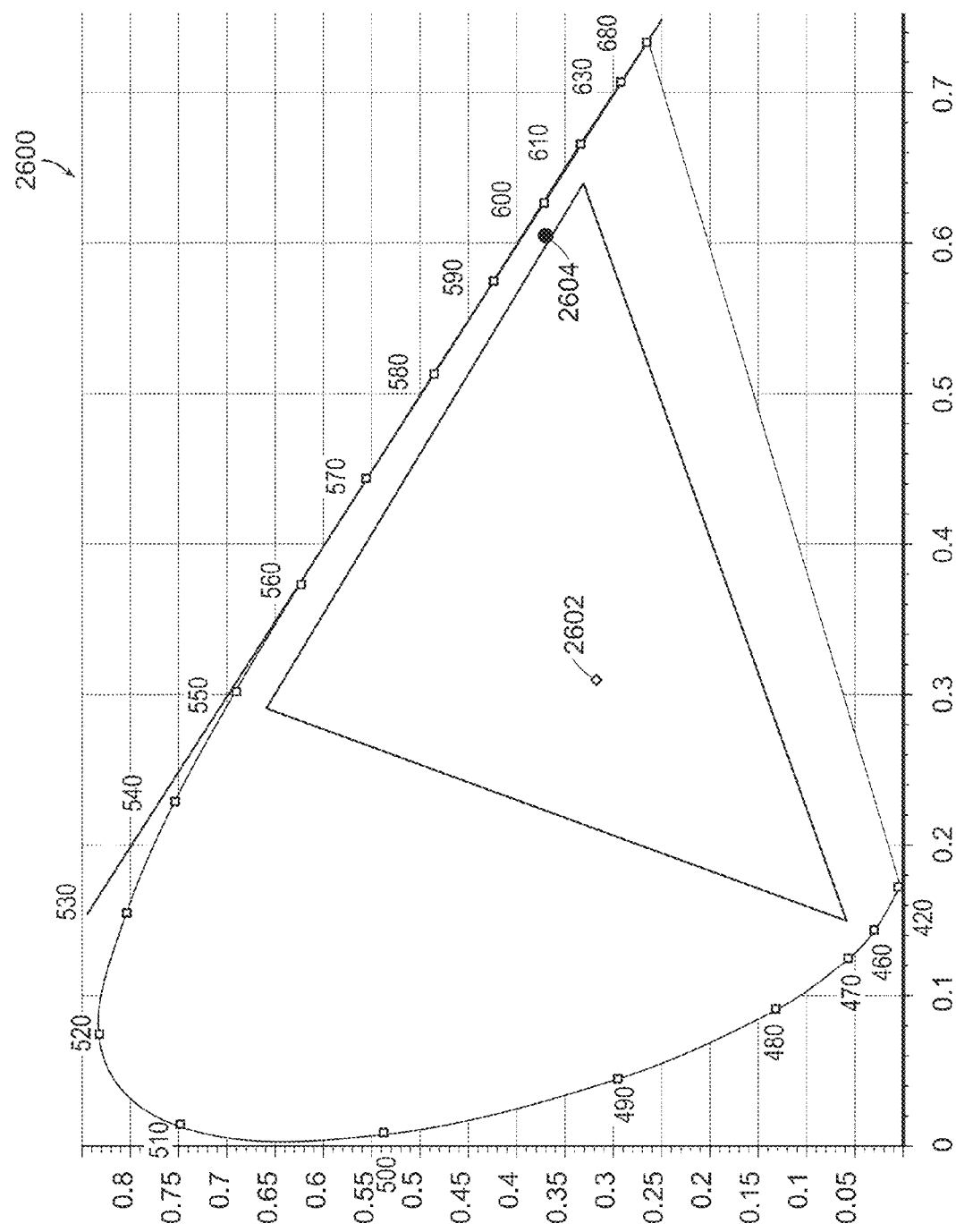

Table 4

| | CIE 1964 Chromaticity Coordinates | | | | | |
|---|---|---|---|---|---|---|
| | Unfiltered | | | Filtered (Notch plus two edge) | | |
| Source | x | y | z | x | y | z |
| Red LCD | 0.6 | 0.36 | 0.03 | 0.5 | 0.35 | 0.09 |
| Green LCD | 0.15 | 0.03 | 0.8 | 0.12 | 0.11 | 0.77 |
| Blue LCD | 0.29 | 0.65 | 0.06 | 0.3 | 0.57 | 0.11 |
| White LCD | 0.28 | 0.32 | 0.39 | 0.35 | 0.36 | 0.29 |

FIG. 28

Table 5

| | CIE 1976 Uniform Color Space Coordinates and Color Difference | | | | | | |
|---|---|---|---|---|---|---|---|
| | Unfiltered | | | Filtered (Notch plus two edge) | | | |
| Source | $u^*$ | $v^*$ | $L^*$ | $u^*$ | $v^*$ | $L^*$ | $\Delta E^*(u^*,v^*)$ |
| Red LCD | 245.4 | 97.0 | 94.2 | 219.3 | 105.6 | 78.1 | 31.8 |
| Green LCD | -111.8 | 145.4 | 98.0 | -85.3 | 127.7 | 86.1 | 34.1 |
| Blue LCD | -1.4 | -64.5 | 96.7 | -11.3 | -29.5 | 88.5 | 37.3 |
| White LCD | -31.5 | -1.6 | 96.0 | 12.6 | 36.2 | 70.4 | 63.5 |

Table 6

| | CIE 1976 Uniform Color Space and Color Difference | | | | | | |
|---|---|---|---|---|---|---|---|
| | Unfiltered | | | Filtered (Notch only) | | | |
| Source | $u^*$ | $v^*$ | $L^*$ | $u^*$ | $v^*$ | $L^*$ | $\Delta E^*(u^*,v^*)$ |
| White LCD | -31.5 | -1.6 | 96.0 | 33.2 | 87.0 | 74.1 | 109.4 |

FIG. 29

LASER PROTECTION EYEWEAR

RELATED APPLICATION SECTION

The present application is a non-provisional application of U.S. Provisional Application Ser. No. 62/001,670, filed on May 22, 2014, entitled "Laser Protection Eyewear". The entire contents of U.S. Provisional Patent Application No. 62/001,670 are herein incorporated by reference.

The section headings used herein are for organizational purposes only and should not to be construed as limiting the subject matter described in the present application in any way.

INTRODUCTION

Handheld laser pointers and other portable laser devices are now widely available, and the market and availability for these products is rapidly growing. Furthermore, high-power (>1 W) hand-held and portable laser devices are becoming widely available at consumer price points that are well under $1,000 USD. Given the rapid advances and continuing commoditization of solid-state laser technology, it is expected that increasingly powerful and affordable hand-held and portable lasers will become available over the next few years. This trend is likely to accelerate over that time.

Pocket-size laser pointers with powers in the 3-5-mW range are capable of producing temporary flash blindness at a distance of a few hundred feet, and are capable of producing distractive glare at distances of approximately 1,000 feet. See e.g., "A look at the hazards of green laser pointers," (www.universetoday.com). Lasers with output powers in the 1-Watt-range have a nominal "ocular hazard distance," the distance of maximal permissible eye exposure, as defined by the American National Standards Institute (ANSI). This distance is in excess of 500 feet. See ANSI-Z136_1. Consequently, it is possible for an individual to voluntarily flash a hand-held or portable laser beam to causes visual distress from a distance that prevents that person from being easily detected. This produces a "laser dazzle," which, as used herein, refers to a laser illumination event experienced directly or indirectly by a victim via a reflection that causes a visual distraction or temporary blindness.

Commercial airline and private pilots report thousands of intentional laser dazzling incidents per year via a United States Federal Aviation Administration incident collection program. There were 1,527 incidents in 2009, 2,836 incidents in 2010, and 3,591 incidents in 2011. See (FAA Laser Safety Website (http://www.faa.gov/about/initiatives/lasers/). This trend is expected to increase. In addition, similar laser dazzle and laser illuminations are aimed at numerous other public safety workers, transportation workers, and athletes. The number of non-aviation-related incidents is not well documented, but predicted to be large.

Laboratory researchers and technicians, medical personnel and patients, and factory and industrial workers use laser safety eye protection for many tasks involving the use of lasers. These applications often require only relatively short-term use of lasers in controlled environments. The time in which an active laser is operating is often on the order of a few minutes or less. Consequently, laser safety eyewear for these applications is not typically designed for comfort and style.

Furthermore, research, medical, and industrial laser applications typically use lasers that emit radiation at a single frequency, or a very narrow band of frequencies, specific to the particular application. FIG. 1 illustrates an absorption spectrum of a known laser safety goggle filter that is used for typical consumer and industrial applications. The known laser safety eyewear used for these applications typically block a much wider bandwidth than necessary, consequently limiting the user's vision by blocking a significant part of the visual spectrum.

BRIEF DESCRIPTION OF THE DRAWINGS

The present teaching, in accordance with preferred and exemplary embodiments, together with further advantages thereof, is more particularly described in the following detailed description, taken in conjunction with the accompanying drawings. The skilled person in the art will understand that the drawings, described below, are for illustration purposes only. The drawings are not necessarily to scale, emphasis instead generally being placed upon illustrating principles of the teaching. In the drawings, like reference characters generally refer to like features and structural elements throughout the various figures. The drawings are not intended to limit the scope of the Applicants' teaching in any way.

FIG. 5 illustrates a Table showing the multilayer thin film profile of the spectral filter profile of FIG. 4.

FIG. 7 illustrates a Table showing the multilayer thin film profile of the spectral filter profile of FIG. 6.

FIG. 9 illustrates a Table showing the multilayer thin film profile of the spectral filter profile of FIG. 8.

FIG. 11A illustrates an embodiment of a lens shape design viewed from the side that accommodates a wide range of vertical input angles of laser light, where the lens shape has a gradual curve that starts at zero degrees as measured from the normal to the plane of the face.

FIG. 11B illustrates an embodiment of a lens shape design viewed from the side that accommodates a wide range of vertical input angles of laser light, where the lens shape has three distinct angles: 0°, 20°, and −40°.

FIG. 11C illustrates an embodiment of a lens shape design viewed from the side that accommodates a wide range of vertical input angles of laser light, where the lens shape has a large region of zero-degree incidence and an angle of −20°.

FIG. 26A illustrates the chromaticity coordinate for a red LCD spectrum.

FIG. 28 illustrates a table listing chromaticity coordinates.

FIG. 29 illustrates two tables listing color difference.

DESCRIPTION OF VARIOUS EMBODIMENTS

Reference in the specification to "one embodiment" or "an embodiment" means that a particular feature, structure, or characteristic described in connection with the embodiment is included in at least one embodiment of the teaching. The appearances of the phrase "in one embodiment" in various places in the specification are not necessarily all referring to the same embodiment.

It should be understood that the individual steps of the methods of the present teachings may be performed in any order and/or simultaneously as long as the teaching remains operable. Furthermore, it should be understood that the apparatus and methods of the present teachings can include any number or all of the described embodiments as long as the teaching remains operable.

The present teaching will now be described in more detail with reference to exemplary embodiments thereof as shown in the accompanying drawings. While the present teachings are described in conjunction with various embodiments and examples, it is not intended that the present teachings be limited to such embodiments. On the contrary, the present teachings encompass various alternatives, modifications and equivalents, as will be appreciated by those of skill in the art. Those of ordinary skill in the art having access to the teaching herein will recognize additional implementations, modifications, and embodiments, as well as other fields of use, which are within the scope of the present disclosure as described herein.

The conventional laser safety eyewear solution typically relies on eyewear in the form of goggles, glasses, or visors that provide greater than optical density 2 (OD2) blocking of the laser wavelength. Optical density 2 means a reduction of the optical power at the laser wavelength of two orders of magnitude, which is a factor of one hundred reduction in optical laser power, or, equivalently, 20 dB reduction in optical power. State-of-the-art laser protection eyewear for consumer and laboratory uses are largely based on passive optical filtering using color-dye-infused or coated plastic lenses. The advantage of the color-dye-infused or coated-lens approach is that it is relatively easily and inexpensive to manufacture. This type of laser protection eyewear is very affordable for these markets. However, dye-based absorbers have particularly wide wavelength blocking regions, and thus exhibit significant reductions in visible light transmission. In addition, large spectral blocking causes significant colorization of the lenses intended for visible laser light (e.g. laser pointers). Specifically, these lenses are significantly red, yellow, blue, green, or brown in color. As a result, color discrimination for normal viewing is severely disrupted. Long-term use of such laser safety glasses affects color balance of vision after removal.

Figure 1:
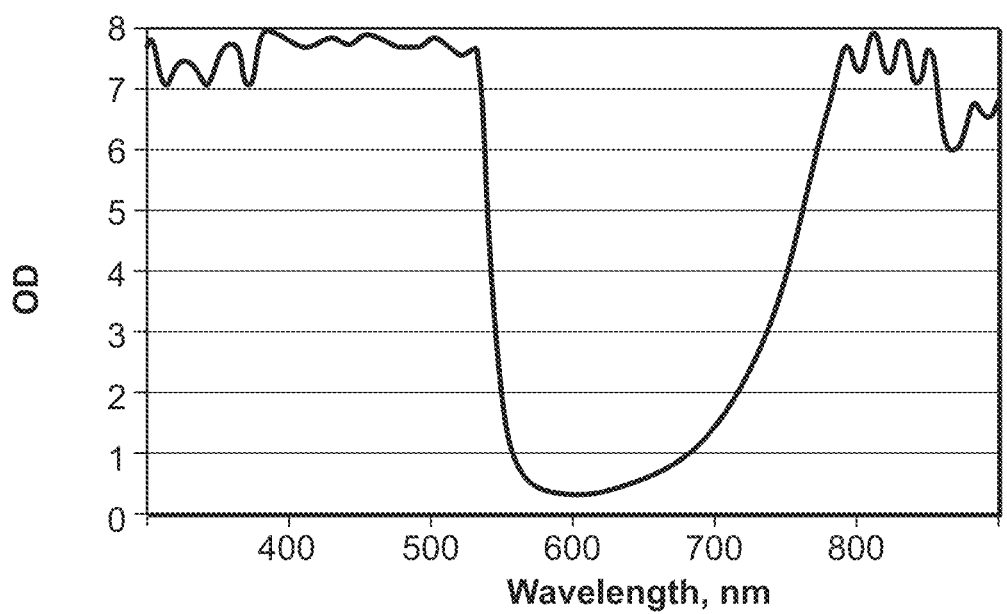
FIG. 1 illustrates an absorption spectrum of a known laser safety goggle filter that is used for typical consumer and industrial applications.
Figure 2:
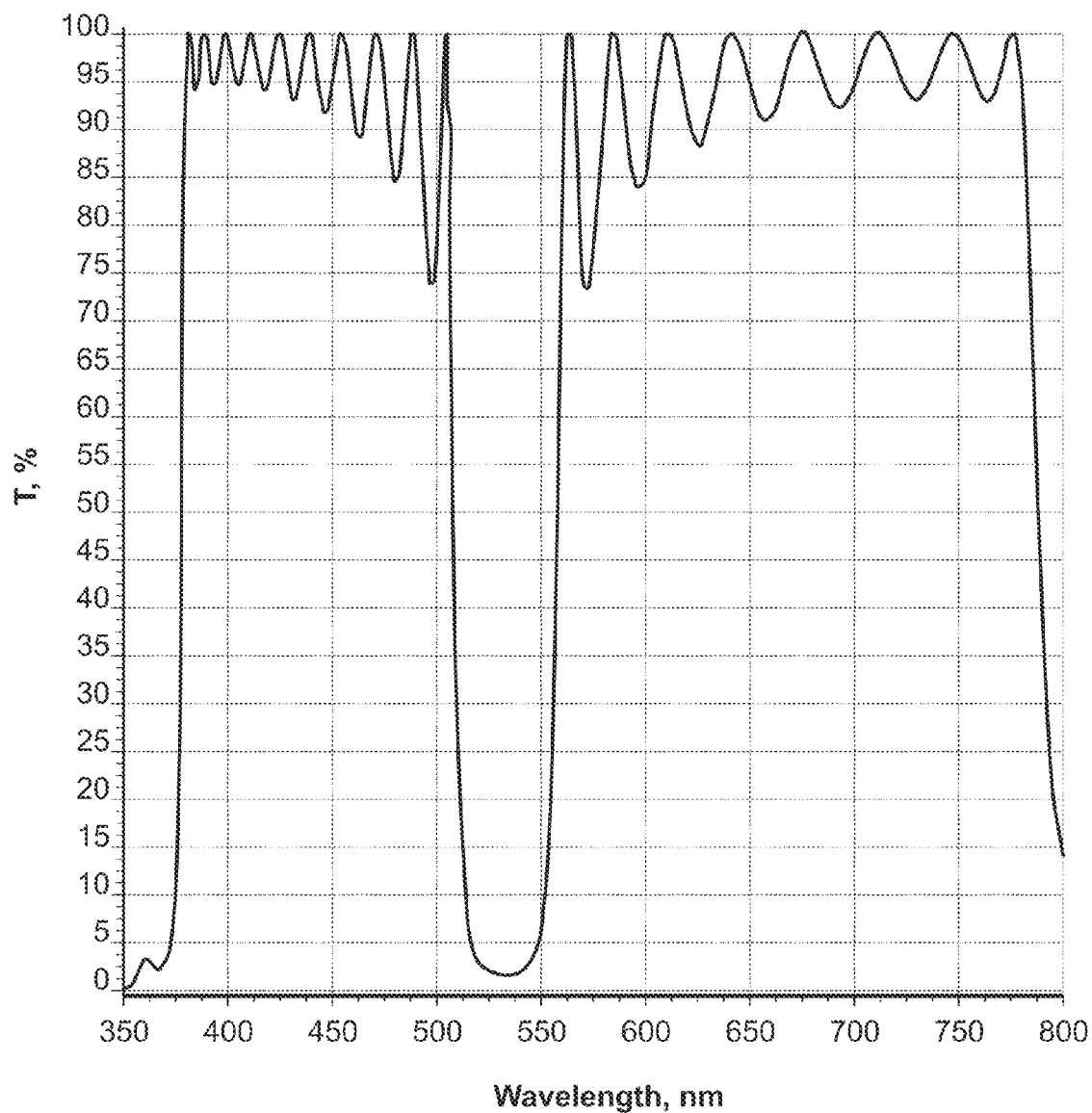
FIG. 2 illustrates a green notch spectral profile of the prior art.

Multilayer interference filters are also known in the art and can be used to block laser light. FIG. 2 illustrates a green notch spectral filter profile from prior art laser blocking technology.

Laser safety eyewear is also needed for numerous military applications. These military applications demand coverage for a wide variety of laser sources found on the battlefield, including infrared laser sources with very high peak-power pulsed and continuous wave operation.

Numerous technologies have been developed to address the threats presented in military applications. These technologies include advanced passive optical filters using, for example, multilayer filters, holographic filters, and nanoparticle filters. See e.g., Donval, "Anti-dazzling protection for air-force pilots" (2012). The technologies for military applications also include active nonlinear optics systems, which are particularly suitable for very high peak powers. These are often employed at the focus of a camera, binocular, or other imaging system. Other suitable technologies include active sense-and-deflect approaches. All of these technologies are costly, and none have managed to reach a price point that would address a consumer market.

What is needed is a consumer-grade, long-term-wearable, laser protection eyewear solution that provides full laser protection in the form of optical blocking of the laser light from hand held laser and laser pointer illumination sources, with none of the disadvantages of the current art.

This teaching relates generally to consumer-grade laser protection eyewear from handheld and portable laser devices. One aspect of the present teaching is that laser protection eyewear provides good visibility and color balance, while maintaining the common features of style and practicality expected from traditional high quality eyewear. In various embodiments according to the present teaching, laser protection eyewear filters particular wavelengths of light from available, and soon-to-be-available, hand-held and portable laser devices to an eye-safe power level.

Additionally, in various embodiments, laser protection eyewear is specifically shaped to block various likely angles of incidence associated with general applications or specific applications (e.g., aircraft take off and landing). The laser protection eyewear frames according to the present teaching fix the protective lenses to the user's head, and are comfortable and wearable for long periods of time. The term "User," as defined herein, includes any person or thing wearing laser protection eyewear to protect against incident laser light.

In addition, the laser protection eyewear of the present teaching can provide common eyewear features such as anti-glare, polarization, abrasion resistance, environmental resistance, support for corrective prescription, and sun protection.

Another aspect of the present teaching is that specific applications, such as aviation and safety, require laser protection eyewear that will not significantly impair the ability to view instrumentation and informational lighting, including cockpit instrumentation panel lights, head-up displays, and lighting for navigation and signage that is external to the vehicle. Many embodiments of the laser protection eyewear of the present teaching are uniquely engineered so that they do not hamper the ability to see common display technology, including handheld devices, computer monitors, and video screens. Many embodiments of the laser protection eyewear of the present teaching are uniquely engineered so that they do not affect the color discrimination of a user viewing common display technology, including handheld devices, computer monitors, and video screens. In other words, the spectral profile of the filters is specifically designed in some embodiments to maintain acceptable color balance for specific viewing purposes, such as safety and navigation.

Yet another aspect of the present teaching is that the laser protection eyewear can provide a spectral filter profile that stimulates wellbeing for the user through color visual stimulation. Light stimulation and spectrally selective light stimulation can reduce depression, increase sleep quality and duration, enhance alertness, reduce jet lag, promote infant weight gain, impact brain activity, and potentially reduce cancer risk. Rea, M., "A second kind of light," OPN, (2006) (herein incorporated by reference); See also, Gvozdev, S. M., "Possibilities of adjusting the light characteristics of illuminating devices based on white and colored LEDs," J. Opt. Technol., (2010) (herein incorporated by reference); Zukauskas, A., "Optimization of solid-state lamps for photobiologically friendly mesopic lighting," Applied Optics (2012) (herein incorporated by reference).

One application of the laser protection eyewear of the present teaching is for protection against the laser pointer devices that are now relatively inexpensive and ubiquitous. The difficulty in protecting against these devices is that they have widely varying wavelengths and power levels. State-of-the-art laser pointers most commonly emit red, green or blue light. Green laser pointers are based on a frequency-doubled, diode-pumped, solid-state laser technology. The lasing wavelength of the Nd-YAG, Nd-YLF or Nd—$YVO_4$ solid-state material used in these lasers is fixed at 1064 nm because of the chemical properties of the neodymium dopant material. Therefore, the wavelength of green laser pointers is a predictable and repeatable 532 nm. In addition, these green battery-powered hand-held laser devices emit radiation at 1064-nm infrared. The combination of green and infrared radiation in these lasers produces optical powers in excess of the 1 W range.

Red laser pointers and many other red handheld and portable laser devices are based on gallium-aluminum-arsenide semiconductor-alloy diode laser technology. Protecting against these laser devices is more challenging because different gallium-aluminum-arsenide semiconductor-alloy alloys have different electron-transition bandgaps based on the ratio of gallium to aluminum in the alloy. The different bandgaps cause different laser emission wavelengths in the red region of the spectrum. Even though the devices appear to emit laser light with a similar color, they have a wide operating wavelength range that is from about 620 nm to 680 nm. In addition, individual laser pointers may emit a single wavelength or may emit several lasing frequencies whose range typically covers 2-10 nm of bandwidth. These lasers typically emit output powers in the range of a few milliwatts to several hundreds of milliwatts.

Blue laser pointers and many other blue handheld and portable laser devices are based on either frequency-doubled diode-pumped solid-state lasers or on gallium-indium-nitride-based semiconductor alloys. The frequency-doubled diode-pumped solid-state lasers operate at a higher harmonic of the Nd-doped solid state materials than the green laser pointers described above. The blue frequency-doubled solid state devices emit at a single wavelength of 473 nm, which is a frequency doubling of the 946-nm emission of the solid state material. Because these single-frequency blue laser devices operate at a higher harmonic than the green-laser counterparts, their output power is typically lower. Other blue handheld laser devices, based on gallium-indium-nitride-based alloys, produce a range of frequencies based on their chemical composition, as in the case of red-emission diode laser materials. These devices are highly efficient at converting electrical power into photons, and can have very high optical output powers. As a result, blue laser pointers emit at a range of frequencies including 445 nm and shorter wavelengths.

Violet laser pointers and many other blue handheld and portable laser devices are based on either gallium nitride, or frequency-doubled infrared versions of the gallium aluminum arsenide devices used to make red laser pointers. Gallium-nitride-based devices operate at 405 nm. Frequency-doubled gallium aluminum arsenide devices operate at a range of frequencies, most commonly 404-406 nm. Both of these types of violet laser devices are modestly high power, with state-of-the-art devices emitting few hundred milliwatts. The wavelength-doubled versions may also emit infrared laser light, yielding total output powers that are in the 1-W range.

The technology used in various handheld laser devices causes their spectral emission to be concentrated in particular regions of the visible spectrum and the infrared and ultraviolet regions that surround the visible region. In particular, there is a range of emissions in the red region of the spectrum and into the infrared, as well as a range of emissions from the blue and into the ultraviolet region of the spectrum. There are also specific emission frequencies in the visible region, particularly a very common and high power emission at 532 nm, and a lower power, and less common emission, at 473 nm. Consequently, in some embodiments, the laser protection eyewear of the present teaching will have a filter spectral profile that blocks a range of frequencies in the red-region of the spectrum, a range of frequencies in the blue range of the spectrum, and will provide a narrow-band notch with high attenuation (20 db or greater) that blocks the green laser wavelength. Attenuation for the purposes of this disclosure can be achieved by any means, including reflection and absorption.

In other embodiments, the laser protection eyewear of the present teaching will have a notch at 532 nm, a notch at 445 nm, and a notch at 650 nm that attenuates at least 10 db or that attenuates at least 20 db. In still other embodiments, the laser protection eyewear of the present teaching will have only one notch at 532 nm and that notch will provide attenuation that is at least 10 db or at least 20 db. In yet other embodiments, the laser protection eyewear of the present teaching will have one or more notches at 408, 445, 473, 532, 445, 650, and 1064 nm. In various embodiments, some or all of these notches provide attenuation that is at least 10 db or at least 20 db. In yet other embodiments, the laser protection eyewear of the present teaching will have shortwave-pass filters with edges ranging from 610-680 nm that attenuate blocked wavelengths at least 10 db. Other embodiments of the laser protection eyewear of the present teaching will have longwave-pass filters with edges ranging from 404-450 nm that attenuate blocked wavelengths at least 10 db. In numerous other embodiments, the laser protection eyewear of the present teaching will include various combinations of edge and notch filters.

A notch filter provides a deep narrowband attenuation region around a particular wavelength of interest. For the laser protection from green laser devices, a notch filter centered at 532 nm is desired. For other laser devices, the center wavelength of the notch can be located at other wavelengths. In general, it is desirable that the bandwidth of the notch region of high attenuation be as narrow as possible to isolate the laser frequencies and limit the amount of visible light being filtered. This minimizes the loss of brightness and spectral illumination bandwidth experienced by the user. However, there is an engineering tradeoff with respect to the number of layers, number of different material compositions, number of different layer thicknesses, and overall thickness of the multilayer thin film profile. The multilayer thin film profile is the complete description of the various layers, including thickness and material composition and/or refractive index, which constitute the filter. In general, larger overall thickness, more layers, and a larger number of different material compositions are required to achieve narrower bandwidth.

One aspect of the present teaching is the understanding that the bandwidth and transition wavelength of the spectral profile of the filter for laser protection eyewear must accommodate the fact that the spectral features of the filter will move to shorter wavelengths as the input angle of the laser light is increased with respect to normal incidence of that filter.

Figure 3:
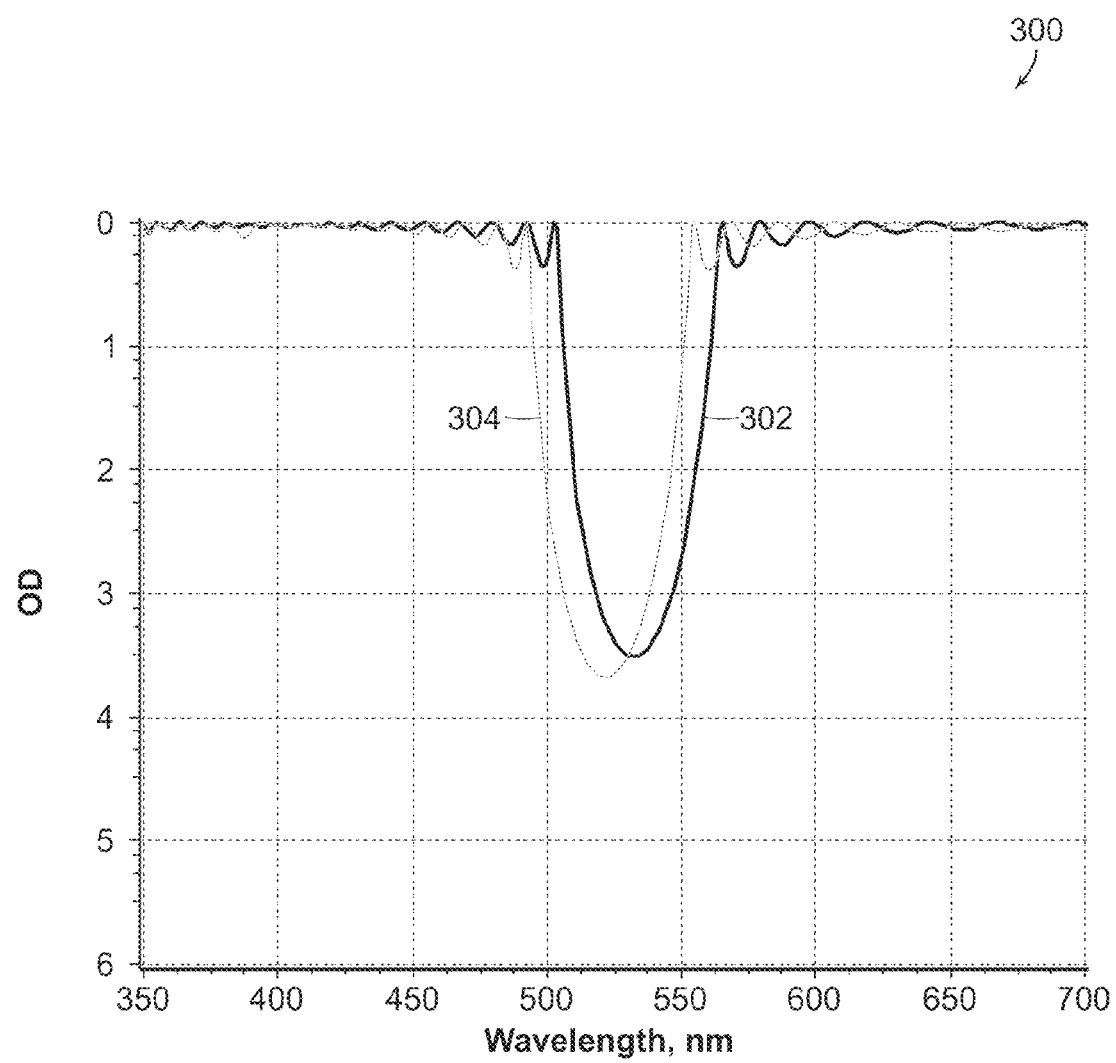
FIG. 3 illustrates a spectral profile of a multilayer notch filter according to the present teaching with incident light angles of zero and twenty degrees as measured from normal incidence.

FIG. 3 illustrates a spectral profile 300 of a multilayer notch filter according to the present teaching with incident light angles of zero 302 and twenty degrees 304, as measured from normal incidence to the plane of the filter. The spectral profile 300 indicates a shift of about twelve nanometers over the twenty-degree range. The shift moves to shorter wavelengths as the function of angle, whether the angle of incidence is positive or negative (as measured from the normal). Therefore, in some embodiments of filters according to the present teaching, a blocking spectral transition region of between ten to thirty nanometers in wavelength, or a notch bandwidth of ten to thirty nanometers, is acceptable for the particular protection application. Such a transition region size can be realized using a relatively easily manufacturable filter design. In addition, in some embodiments of the filter according to the present teaching, the center wavelength of the notch filter is designed to be at slightly longer wavelengths than the laser wavelength for normal incidence radiation to accommodate different angles of incidence.

Similarly, edge filters, such as the edge filters described further below, exhibit additional wavelength blocking in the red region of the spectrum at larger angles of incident laser light with respect to the normal of the filter, because of a shift of the spectral filter profile toward shorter frequencies. The spectral blocking at large angles of incident laser light can block orange and yellow wavelengths, as well as red. Therefore, some embodiments of the filter will target a longer wavelength for the transition to the blocking region at normal incidence in the red region of the spectrum. In addition, edge filters in the blue region of the spectrum exhibit reduced blocking of the blue and blue-green region of the spectrum at higher angles of incident laser light with respect to the normal of the filter. Therefore, some embodiments of the filter according to the present teaching will utilize a shorter wavelength for the blocking region at normal incidence in the blue region of the spectrum. In these different embodiments, the filter will block the laser frequencies of interest at larger incident angles, even though there is a shift in the wavelength for transition at large angles of laser light incident with respect to the normal to the plane of the filter.

Edge pass filters transition from low attenuation to high attenuation over a narrow range of spectrum at a particular wavelength. The region of changing attenuation can run from shorter wavelengths to longer wavelengths in a shortwave-pass edge filter, and from longer wavelengths to shorter wavelengths in a longwave-pass filter. For laser protection applications, protecting against red laser radiation would require a shortwave-pass filter with a transition wavelength of approximately 610-615 nm. Protecting against blue laser radiation requires a longwave-pass filter with a transition wavelength around 440 nm. In many embodiments, it is desirable to have the transition bandwidth be as narrow as possible to isolate the laser frequencies and to limit the amount of visible light being filtered—thereby maximizing the light available to the user.

There are several engineering tradeoffs between layer thickness and complexity of the multilayer thin film profile that determine the transition bandwidth. Furthermore, the bandwidth and transition wavelength that determine the transition bandwidth must accommodate the fact that the filter spectral features will move to shorter wavelengths as the input angle of the laser light is increased with respect to normal incidence. In general, a transition region between 5-15 nm is acceptable for laser protection applications, and such a transition region can be realized using a relatively easily manufacturable filter design.

In some embodiments, two edge filters are constructed using a single visible band pass filter from a single layer structure. In other embodiments, separate edge filters are constructed for the red region and for the blue region using separate shortwave and longwave-pass edge filter multilayer thin film profile designs, respectively. These two edge filter designs may be coated on the same side or on different sides of the eyewear lens, depending on the embodiment.

A multilayer filter design can be synthesized for a particular substrate material and for a particular set of at least two thin film layer materials with different refractive indices. The terms "lens" and "substrate" are used interchangeably herein. For the laser protection application, the substrates are made from optically transparent material. "Optically transparent material," as used herein, refers to materials that have optical transmission generally greater than 50% over some fraction of the visible spectrum, but for some applications it may be as low as 10%. Specific layer thickness profiles are rendered using a combination of well-known mathematical properties of light propagation through multilayer thin films, together with known techniques of optimization against a target spectral profile. Other optimization parameters, such as filter thickness, number of layers, and/or other properties, are also used. Ultimately, a multilayer thin film profile is established that best meets a target spectral profile. In general, there are several multilayer thin film profiles that can be used to realize most desired spectral profiles to within a particular optimization objective. Therefore, filter specifications are driven largely by the desired spectral profile. Of course, manufacturability and reliability concerns favor filter layer thickness profiles with a relatively few number of layers, relatively similar layer thicknesses, and overall smaller thickness of the multilayer thin film profile.

Figure 4:
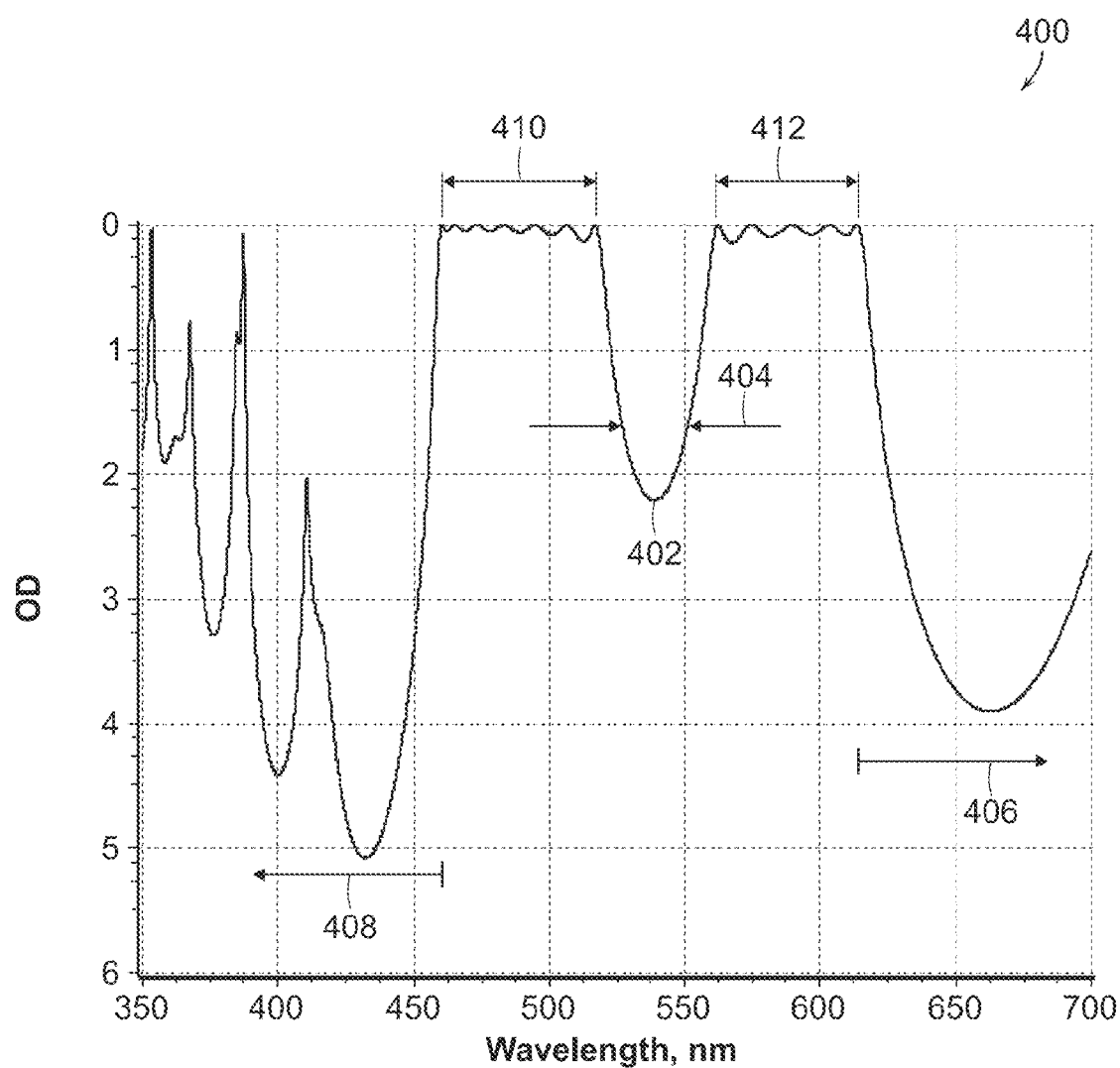
FIG. 4 illustrates an embodiment of a spectral filter profile for a filter that blocks blue, violet, green, and red laser devices, according to the present teaching.

FIG. 4 illustrates an embodiment of a spectral filter profile 400 of a filter according to the present teaching for laser protection applications that blocks blue, violet, green and red laser devices. This spectral filter profile embodiment exhibits a notch 402 with high attenuation centered at 532 nm with a bandwidth 304 of approximately 25 nm. It also exhibits two regions of high attenuation, one in the red region of the spectrum 406 at wavelengths longer than about 610 nm, and another in the blue region of the spectrum 408 at wavelengths shorter than about 450 nm. This spectral filter profile embodiment exhibits high transmission throughout the remainder of the visible spectrum and has very few spectral features across the high transmission region 410, 412. For purposes of this disclosure, this particular spectral filter profile is referred to as notch-plus-two-edges. The particular spectral filter profile embodiment of FIG. 4 is constructed in a multilayer thin film embodiment using a polycarbonate substrate material with a refractive index of 1.586. The high index thin film layer is tantalum oxide with a refractive index of 2.3 and the low refractive index thin film layer is silicon dioxide with a refractive index of 1.45. There are 47 layers ranging in thickness from 21 nm to 278 nm. The total layer thickness is 3.93 microns thick. FIG. 5 illustrates a table of the resulting multilayer thin film profile.

A wide variety of multilayer thin film profiles can be used to achieve the desired spectral filter profile shown in FIG. 4. For example, one can vary the layer thicknesses, thin film materials, and other parameters from those provided in this example to fine tune the spectral features of the spectral filter profile. Furthermore, it is possible to achieve a single multilayer thin film profile by using two or more individual multilayer thin film profiles. In various embodiments, these multiple thin film profiles may be applied on the same side, or on different sides, of the lens substrate. Applying thin film profiles to both sides of a lens substrate can reduce variations in effective thin film thickness caused by compressive and tensile forces.

Figure 6:
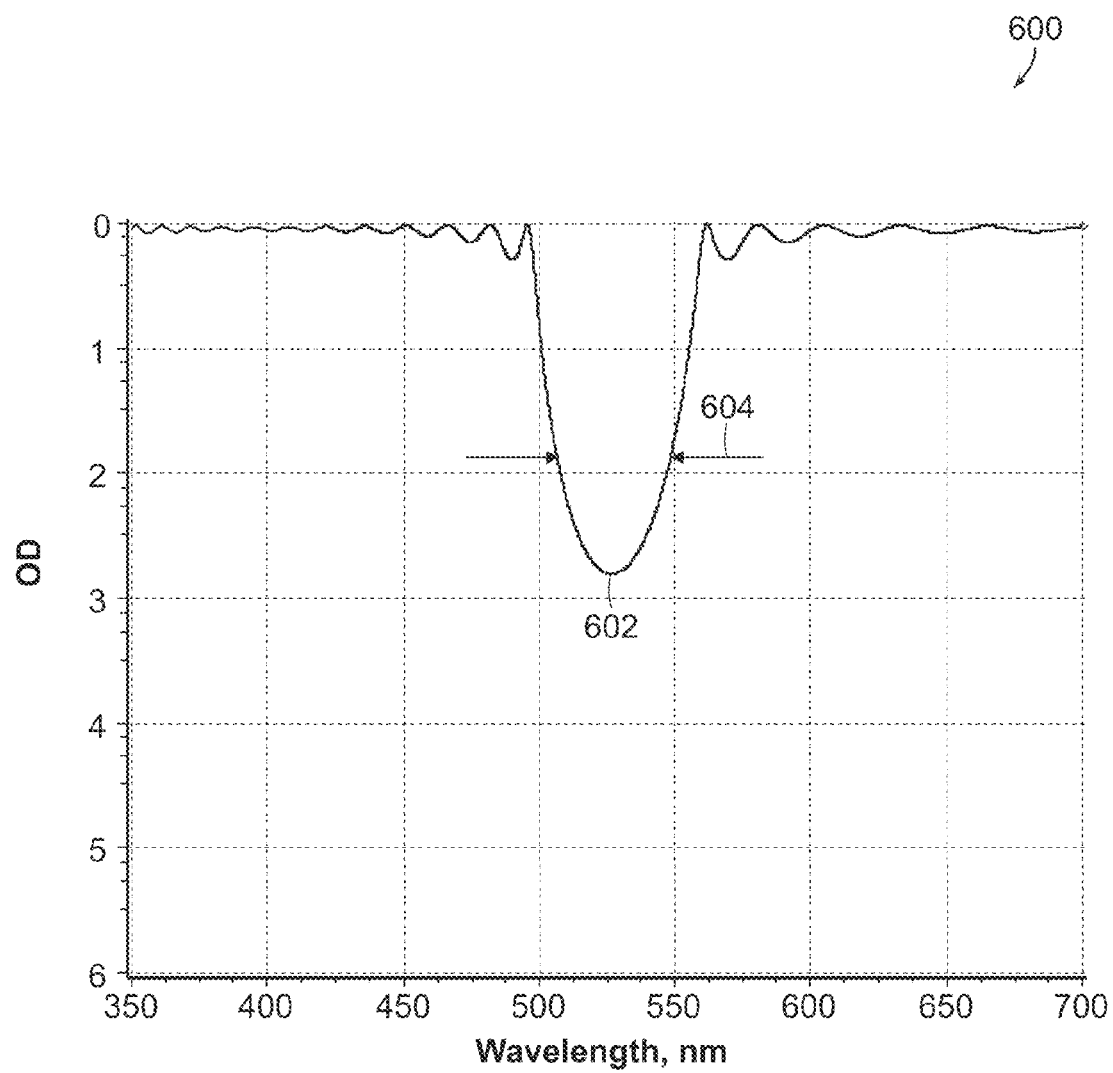
FIG. 6 illustrates an embodiment of a spectral filter profile of a notch filter for laser protection applications, according to the present teaching.

FIG. 6 illustrates an embodiment of a spectral filter profile of a notch filter according to the present teaching for laser protection applications. This spectral filter profile embodiment exhibits a deep attenuation centered around 532 nm 602 with a bandwidth of about 30 nm 604. This spectral filter profile embodiment will block light from green laser sources, which are particularly damaging to human eyes. The particular spectral filter profile embodiment shown in FIG. 6 is constructed in a multilayer thin film embodiment using a polycarbonate substrate material with a refractive index of 1.586. The high index thin film layer is tantalum oxide with refractive index of 2.3 and the low index thin film layer is silicon dioxide with refractive index of 1.45. There are 19 layers with two thicknesses of 173.4 nm and 275.0 nm. The total layer thickness is 4.2 microns thick. FIG. 7 illustrates a table of the multilayer thin film profile. A wide variety of multilayer thin film profiles can be applied to achieve the desired spectral profile shown in this example. In other embodiments, it is possible to vary the layer thicknesses, thin film materials, and other parameters from those provided in this example to fine tune the spectral features of the spectral filter profile.

Figure 8:
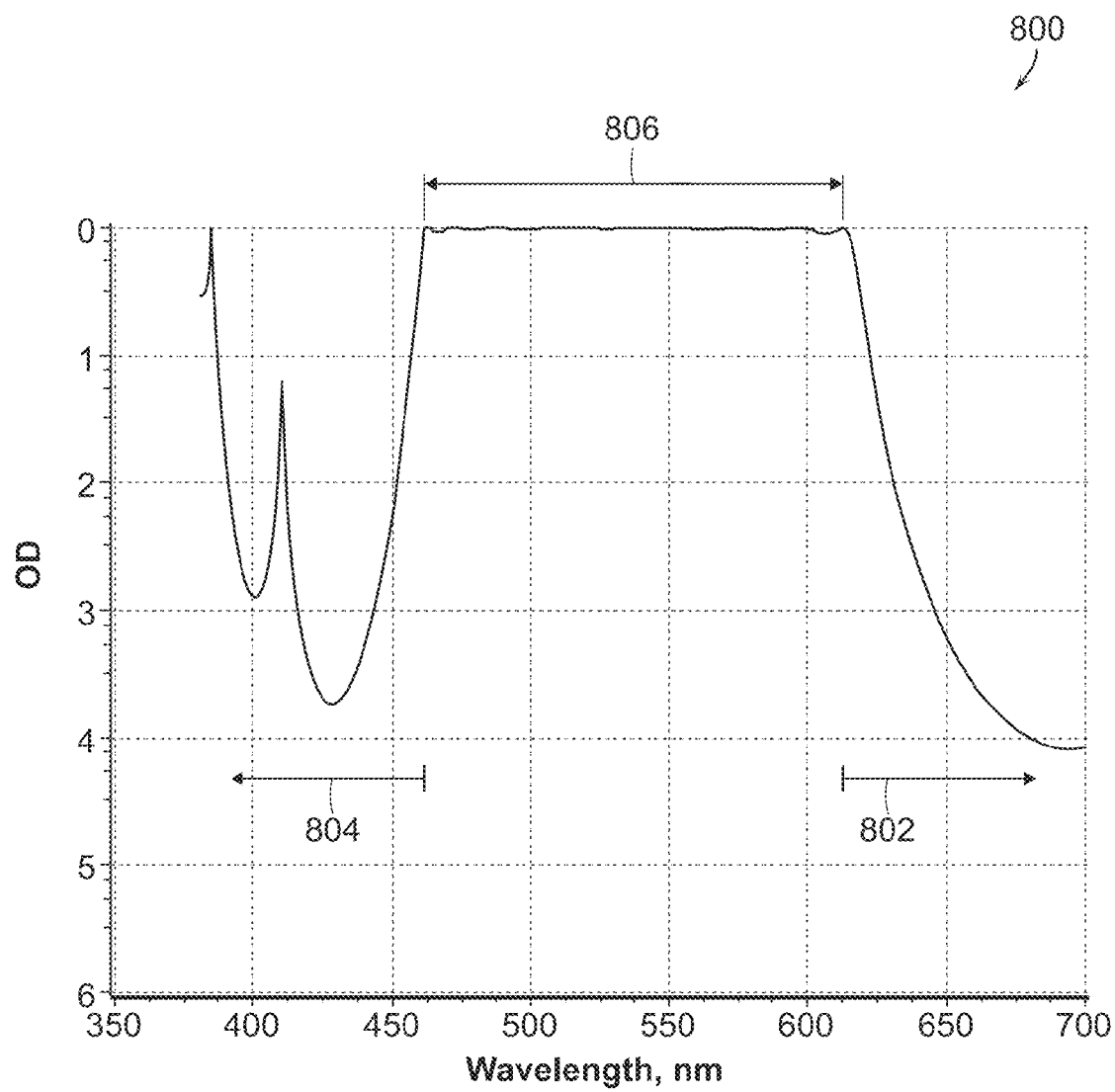
FIG. 8 illustrates an embodiment of a spectral filter profile of a two-edge filter for the laser protection application, according to the present teaching.

FIG. 8 illustrates an embodiment of a spectral filter profile of a two-edge filter 800 for laser protection applications, according to the present teaching. This spectral filter profile embodiment exhibits two regions of deep attenuation, one in the red region of the spectrum 802 at wavelengths longer than about 610 nm, and another in the blue region of the spectrum 804 at wavelengths shorter than about 450 nm. This particular spectral filter profile exhibits high transmission 806 throughout the remainder of the visible spectrum and has very few spectral features across this region. The particular spectral filter profile shown in FIG. 8 uses a polycarbonate substrate material with a refractive index of 1.586. The high index thin film layer is tantalum oxide with refractive index of 2.3 and the low index thin film layer is silicon dioxide with refractive index of 1.45. There are 36 layers with layer thicknesses ranging from 5.2 nm to 206 nm. The total layer thickness is 3.1 microns thick.

FIG. 9 illustrates a table of the multilayer thin film profile. A wide variety of multilayer thin film profiles can be applied to achieve the desired spectral profile shown in this example. A variety of specific filter shapes and profiles may be used in different embodiments for particular laser protection applications. One skilled in the art will appreciate that it is possible to vary the layer thicknesses, thin film materials, and other parameters from those provided in this example to fine tune the spectral features of the spectral filter profile.

A multilayer filter design that includes both red and blue edge filters and a notch in a single layer, will have slightly lower performance than two filters that are designed for a notch, two-edges, or bandpass filtering. This conclusion, however, assumes the total layer thickness and number of layers are comparable. There is an engineering tradeoff between the total layer thickness and the number of thin film layers for the particular spectral features, including the bandwidth of notches and the edges desired for particular applications. Different embodiments of the laser protection eyewear will utilize various combinations of these approaches as appropriate.

Interference filter spectral performance breaks down at angles of incidence greater than approximately twenty degrees. Many laser protection applications, such as laser protection for aviation applications, demands protection for a larger range of input angles than between zero to twenty degrees. One aspect of the present teaching is to provide protection from laser radiation at a variety of angles, with respect to the normal of the plane of the face, in both the horizontal and vertical directions. For the purposes of this disclosure, the "plane of the face" is defined herein as a plane containing a line fixed at the glabella, oriented parallel to a line connecting the center of both eyes, and a line that connects the glabella to the subnasale.

Eyewear frames hold lenses in a substantially fixed position with respect to the plane of the face. Providing a lens with multiple angles with respect to the plane of the face has several advantages. First, the lens blocks a wider range of input laser light angles when the face is in a fixed position. Also, the user can perform head motions, including in and out, up and down, and pitch and yaw, to block any particular input light angle. Very small motions of much less than a ½-inch will allow a user to achieve full angular coverage. As a result, there is no significant change in the field of view and these motions will not disrupt normal tasks.

Figure 10A:
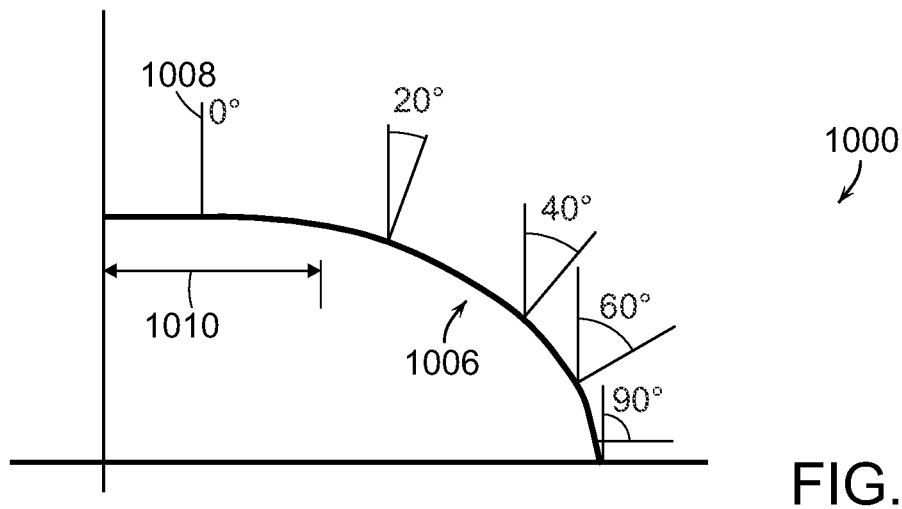
FIG. 10A illustrates an embodiment of a lens shape design viewed from the top that accommodates a wide range of horizontal input angles of laser light, where the lens shape has a gradual curve that starts at zero degrees as measured from the normal to the plane of the face.
Figure 10B:
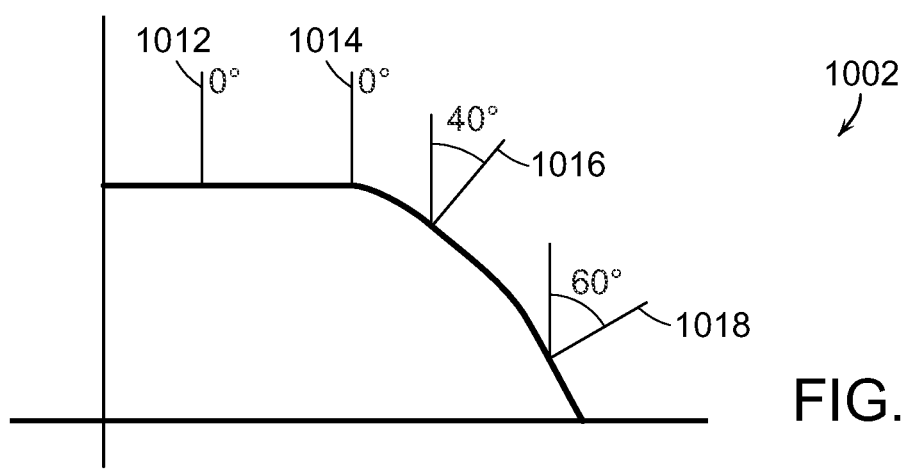
FIG. 10B illustrates an embodiment of a lens shape design viewed from the top that accommodates a wide range of horizontal input angles of laser light, where the lens shape has three distinct angles: 0°, 40°, and 60°.
Figure 10C:
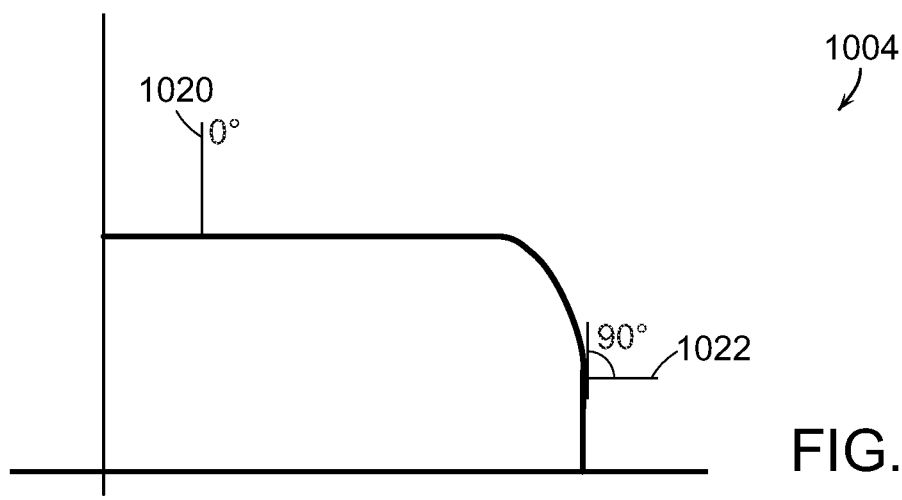
FIG. 10C illustrates an embodiment of a lens shape design viewed from the top that accommodates a wide range of horizontal input angles of laser light, where the lens shape has a large region of zero-degree incidence.

FIGS. 10A-10C illustrate three specific embodiments of lens shape designs viewed from the top that accommodate a wide range of horizontal input angles of laser light. Only the right lens is illustrated for simplicity. One skilled in the art will appreciate that the curve for the left lens is flipped 180° about the center axis. FIG. 10A illustrates an embodiment of a lens shape design 1000 viewed from the top that accommodates a wide range of horizontal input angles of laser light where the lens shape has a gradual curve 1006 that starts at zero degrees 1008, as measured from the normal to the plane of the face. A flat region 1010 extends approximately 1 inch from the inner edge of the lens, where it begins a gradual curve toward the outer edge of the lens. As shown in FIG. 10A, this particular embodiment covers a lens shape that has a substantially continuous ranges of horizontal angles from zero to ninety degrees. This includes twenty degrees, forty degrees, sixty degrees, and ninety degrees. The horizontal angle represents the angle between the normal to the surface of the lens, at a given horizontal position on the lens, and the normal to the plane of the face.

FIG. 10B illustrates an embodiment of a lens shape design 1002 viewed from the top that accommodates a wide range of horizontal input angles of laser light, where the lens shape has three distinct horizontal angles: 0°, 1012, 1014, 40°, 1016 and 60° 1018. FIG. 10B shows a lens shape that is more angular with larger regions of distinct angles that are accessible. This embodiment is advantageous for applications where a gradual lens design is not desirable.

FIG. 10C illustrates an embodiment of a lens shape design 1004 viewed from the top that accommodates a wide range of horizontal input angles of laser light, where the lens shape has a large region of zero-degree horizontal angle 1020. One skilled in the art will appreciate that there are numerous variations of the lens shape designs shown in FIGS. 10A-10C that will accommodate wide ranges of horizontal angles according to the present teaching.

The blocking input angle of laser protection eyewear with a particular interference filter coating can be extended by angling the lens shape with respect to the normal of the plane of the face. An interference filter coating on a flat surface will maintain sufficient spectral integrity to block incident laser light at angles of up to about twenty degrees from the normal to the coating surface. The filter coatings are conformal to the surface of the lens.

Figure 10D:
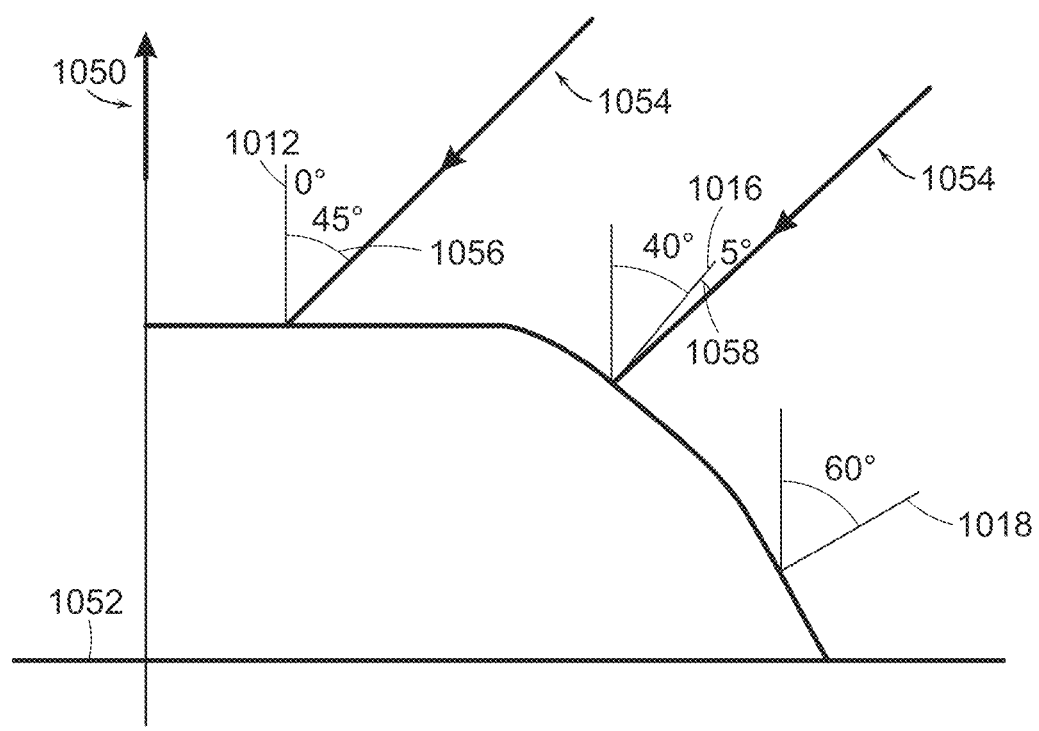
FIG. 10D illustrates an embodiment of a lens shape design and incident laser light.

FIG. 10D illustrates a lens shape embodiment of the present teaching 1002 in the presence of incident laser light 1054. FIG. 10D represents a horizontal lens shape and illustrates a plane of the face 1052, and the normal to the plane of the face 1050, relative to the lens shape. The incident laser light forms an incident light angle with respect to the normal to the plane of the face 1050 of forty-five degrees. On the left hand portion of the lens, this incident light impacts the lens at an angle 1056 of forty-five degrees with respect to the normal to the surface of the lens. This is because the horizontal lens angle 1012 is zero degrees with respect to the normal to the plane of the face. The interference filter may not block an incident light angle of greater than twenty degrees with respect to the surface of the lens, because the filter spectral properties are not adequate at large input angles. Further to the right on the lens shape illustrated in FIG. 10D, the incident light impacts at an angle 1058 of five degrees with respect to the normal to the surface of the lens. This is because the lens angle 1016 is forty degrees with respect to the normal to the plane of the face 1050. An incident light angle of less than twenty degrees with respect to the surface of the lens will be substantially blocked by the filter. Laser protection eyewear, according to this aspect of the present teaching, includes a lens shape that will block laser light aimed at the eyes at angles in the horizontal direction from as much as plus or minus 90 degrees from the normal to the plane of the face.

FIGS. 11A-11C illustrates a set of lens shape designs that accommodates a wide range of vertical input angles of laser light. These figures show three specific embodiments of the vertical lens design viewed from the side. Angles of the normal to the curve of the vertical lens shape are measured with respect to the normal to the plane of the face.

FIG. 11A illustrates an embodiment of a lens shape design 1100 viewed from the side that accommodates a wide range of vertical input angles of laser light, where the lens shape has a gradual curve 1106 that starts at zero degrees 1108 as measured from the normal to the plane of the face. At the top of the lens in FIG. 11A is a gradual curve that starts at sixty degrees 1110 as measured from the normal to the plane of the face. The lens has a zero degree curve at the center of the lens 1108, and then negative angles below the center. This lens shape design extends the angular coverage of the interference filter by plus or minus sixty degrees.

FIG. 11B illustrates another embodiment of the lens shape design 1102. In this design, a substantially flat region of zero curvature is provided at the center of the lens 1112. This region may extend on the order of an inch, depending on the particular application. The top and bottom of the lens have a curvature. The curvatures of the lens shown in FIG. 11B are twenty degrees 1114 and minus forty degrees 1116 on the top and the bottom, respectively.

FIG. 11C illustrates an alternative embodiment of the lens shape design 1104, where the lens has a flat region of zero-degree curvature at the top of the lens 1118, and then curves inward at negative angles at the lower half of the lens 1120. These particular lens angles are illustrative, and a variety of angles are envisioned for different embodiments based on a particular use. One skilled in the art will appreciate that there are many variations of the embodiments shown in FIGS. 11A-11C.

The blocking input angle of laser protection eyewear with a particular interference filter coating can be extended by angling the lens shape in the vertical direction with respect to the normal of the plane of the face. An interference filter coating on a flat surface will maintain sufficient spectral integrity to block incident laser light at angles of up to about twenty degrees from the normal to the coating surface. In the same manner as with the lens shape in the horizontal direction, the lens shape in the vertical direction will provide blocking for incident laser light at angles greater than twenty degrees with respect to the normal to the plane of the face. Laser protection eyewear according to this aspect of the present teaching includes a lens shape that will block laser light aimed at the eyes at angles along the vertical direction from as much as plus or minus sixty degrees from the normal to the plane of the face.

Figure 12:
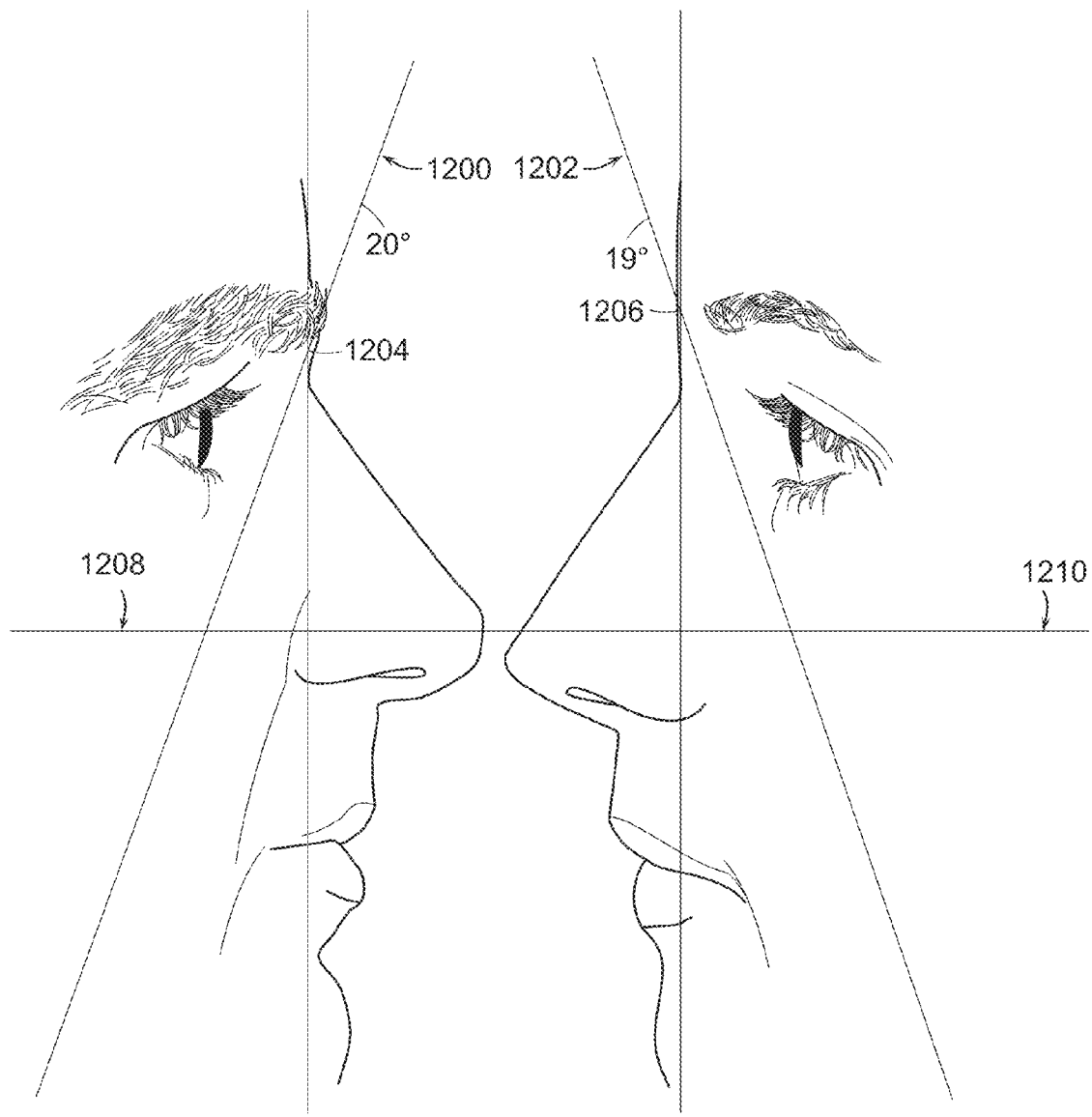
FIG. 12 illustrates the offset angle from the outermost protrusion of the eyebrow to the cheekbone in the human face.

FIG. 12 illustrates the offset angle 1200, 1202 from the outermost protrusion of the eyebrow 1204, 1206 to the cheekbone 1208, 1210 in the human face. A human face has an angle from the outermost protrusion of the eyebrow to the cheekbone, as measured from the normal to the plane of the face. It is an object of this invention to take advantage of this angle to provide better angular protection from input laser light angles. This angle is termed an "offset angle" for the purposes of this disclosure, and is measured from the plane of the face. The offset angle ranges from approximately zero to twenty degrees.

Figure 13C:
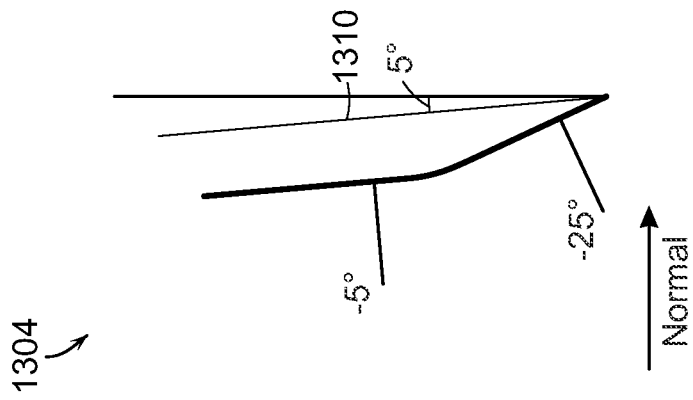
FIG. 13C illustrates an embodiment of a lens shape design viewed from the side that accommodates a wide range of vertical input angles of laser light set at a 5° offset angle, where the lens shape has angles of −5° and −25°.
Figure 13B:
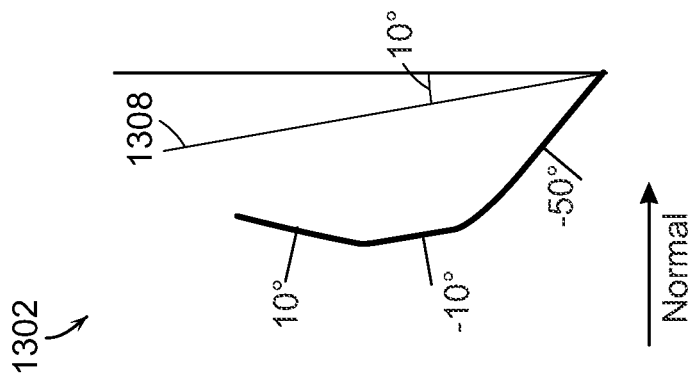
FIG. 13B illustrates an embodiment of a lens shape design viewed from the side that accommodates a wide range of vertical input angles of laser light set at a 10° offset angle, where the lens shape has three distinct angles: 10°, −10°, and −50°.
Figure 13A:
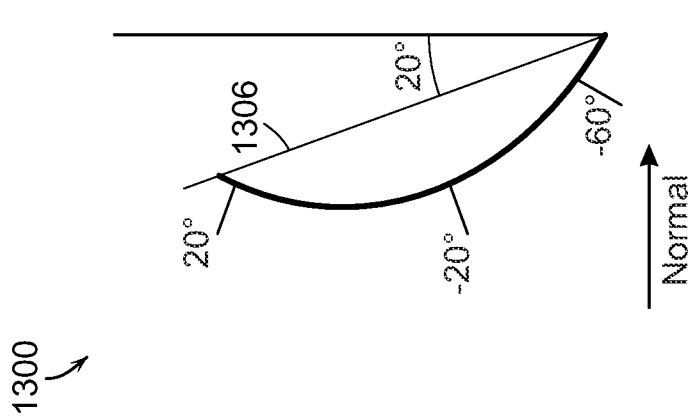
FIG. 13A illustrates an embodiment of a lens shape design viewed from the side that accommodates a wide range of vertical input angles of laser light, where the lens shape has a gradual curve that starts at zero degrees as measured from a 20° offset angle of the face.

FIGS. 13A-13C illustrate vertical lens designs that utilize different lens shape designs, 1300, 1302, 1304 based on particular offset angles of 20° (1306), 10° (1308), and 5° (1310). These particular offset angles are chosen to further illustrate the present teaching and are not intended to limit the invention in any way.

Another feature of the present teaching is that a combination may be used of vertical lens designs with different horizontal lens designs, as well as different offset angles. These various lens design combinations may also include vertical and/or horizontal designs and/or offset angels such as flat vertical lens designs and flat horizontal lens designs.

Figure 14:
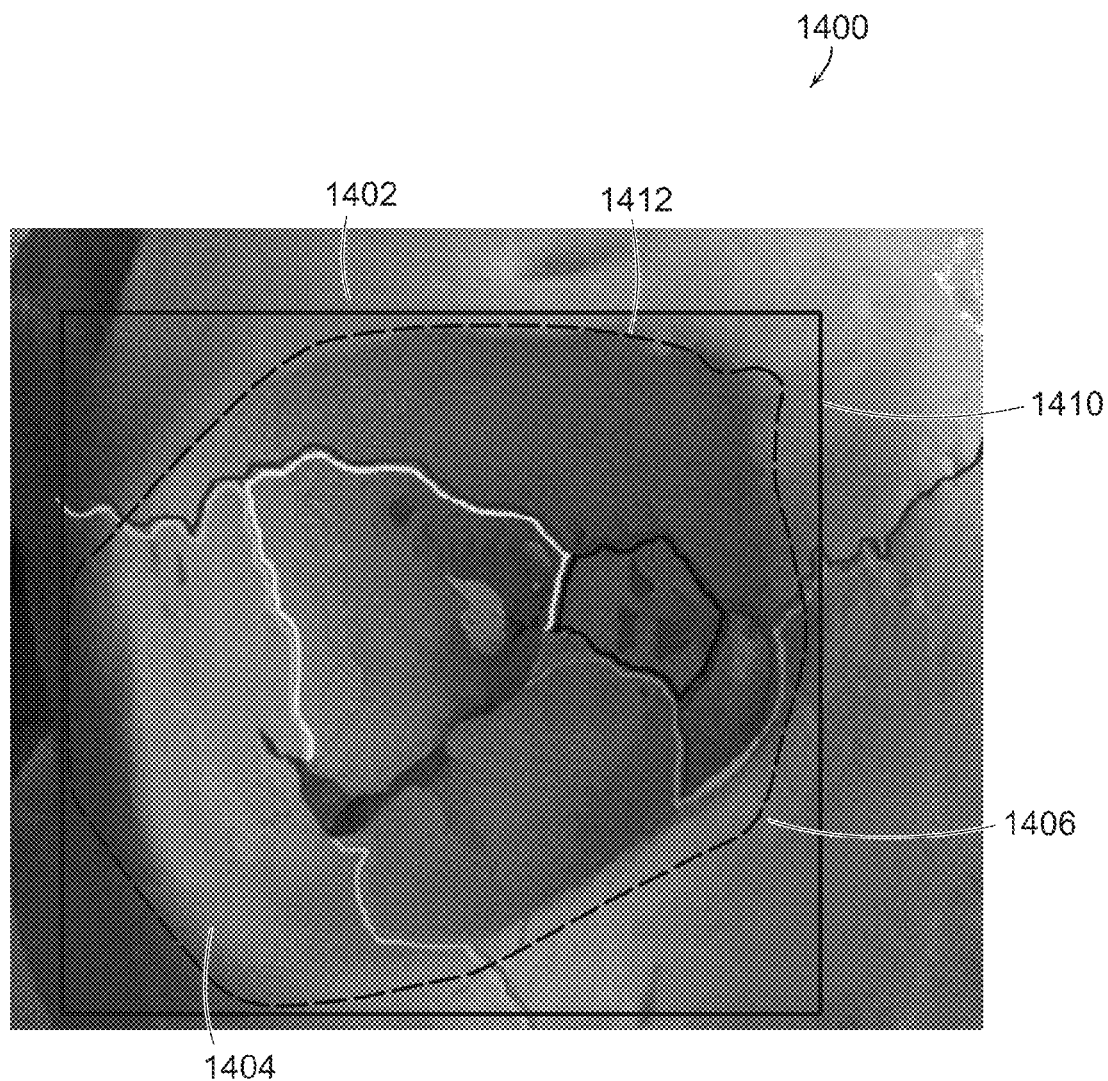
FIG. 14 illustrates the eye socket.

Another feature of the present teaching is that a protective lens design with multiple angles can be molded close to head, cheeks, brow, and other facial features, providing better blocking coverage of the eye. In some embodiments, the lens design is made to follow the contour of the eye socket. The orbit is the cavity or socket of the skull which contain the eye and its appendages. The orbits are either conical or four-sided pyramidal cavities, which open into the midline of the face and point back into the head. As illustrated in FIG. 14, the eye socket 1400 is made up of three bones: the frontal bone 1402, the zygomatic bone 1404, and the maxillary bone 1406. The frontal bone 1402 is on the top and forms the ridge of the eye socket nominally at the line of the eyebrow on the face. The zygomatic bone 1404 forms the side of the eye socket toward the outer edge of the face and below the eye, and the maxillary bone 1406 forms the lower and inner ridge of the eye socket, toward the nose.

FIG. 14 illustrates the eye socket 1400. In an adult, the eye socket is framed by a rectangular region 1410 that is approximately 2.25-2.5 inches wide by 1.5-1.75 inches tall. The eye socket is a natural protective region for the eye. The eye socket ridge 1412, the outermost region of bone surrounding the eye, protrudes in order to help protect the eye from damage. One aspect of the present teaching is that protective eyewear utilizes the natural protective nature of the eye socket. Lenses for protective eyewear according to one embodiment of the present teaching follow the contour of the eye socket ridge.

Figure 15:
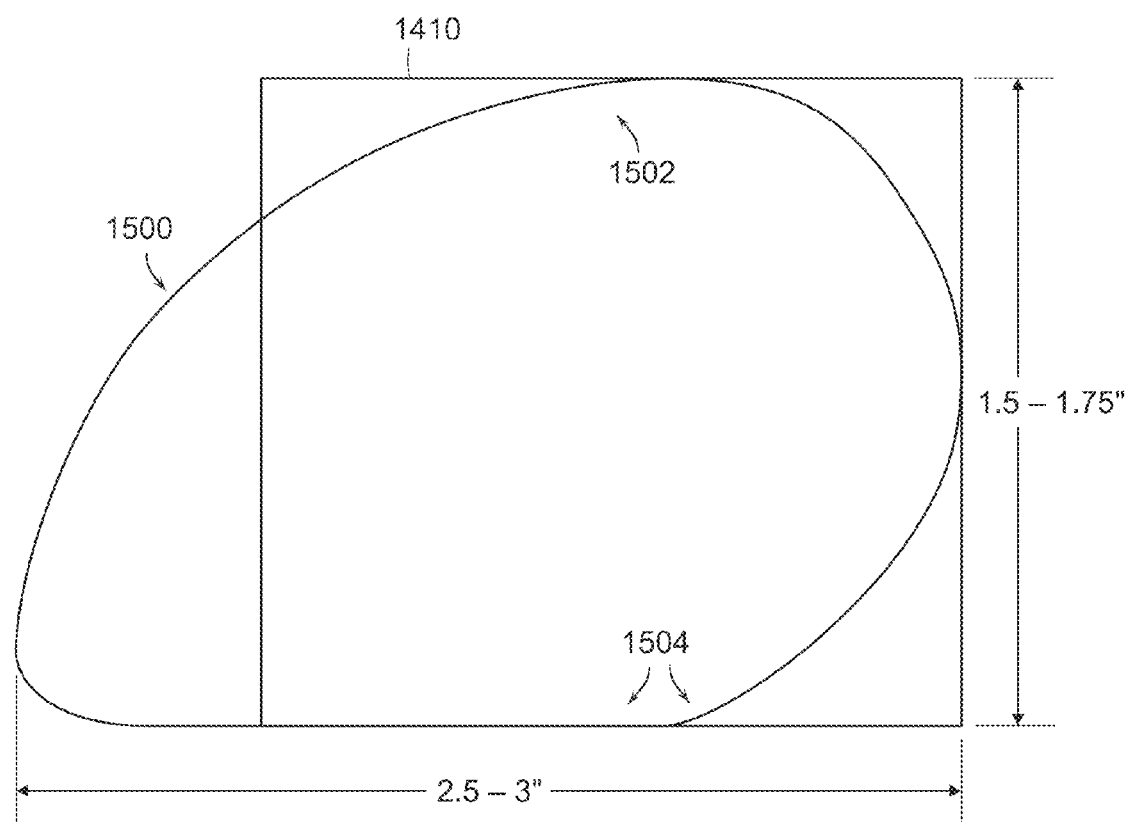
FIG. 15 illustrates an embodiment of a lens design that follows the eye socket contour within the eye socket frame.

Referring to both FIGS. 14 and 15, FIG. 15 illustrates an embodiment of a lens shape perimeter design 1500 that follows the eye socket ridge 1412 contour within the eye socket frame 1410. This figure illustrates the lens perimeter as viewed straight toward the face. For simplicity, a right lens perimeter is shown. One skilled in the art will appreciate that the perimeter for the left lens is flipped 180° from left-to-right across the page. The curvature of the upper 1502 and lower 1504 regions of the lens perimeter is designed to follow a human eye socket ridge. This curvature prevents laser light from entering from the area right outside of the lens area because the light is blocked by the brow, cheeks, nose, and side of the face.

Figure 16:
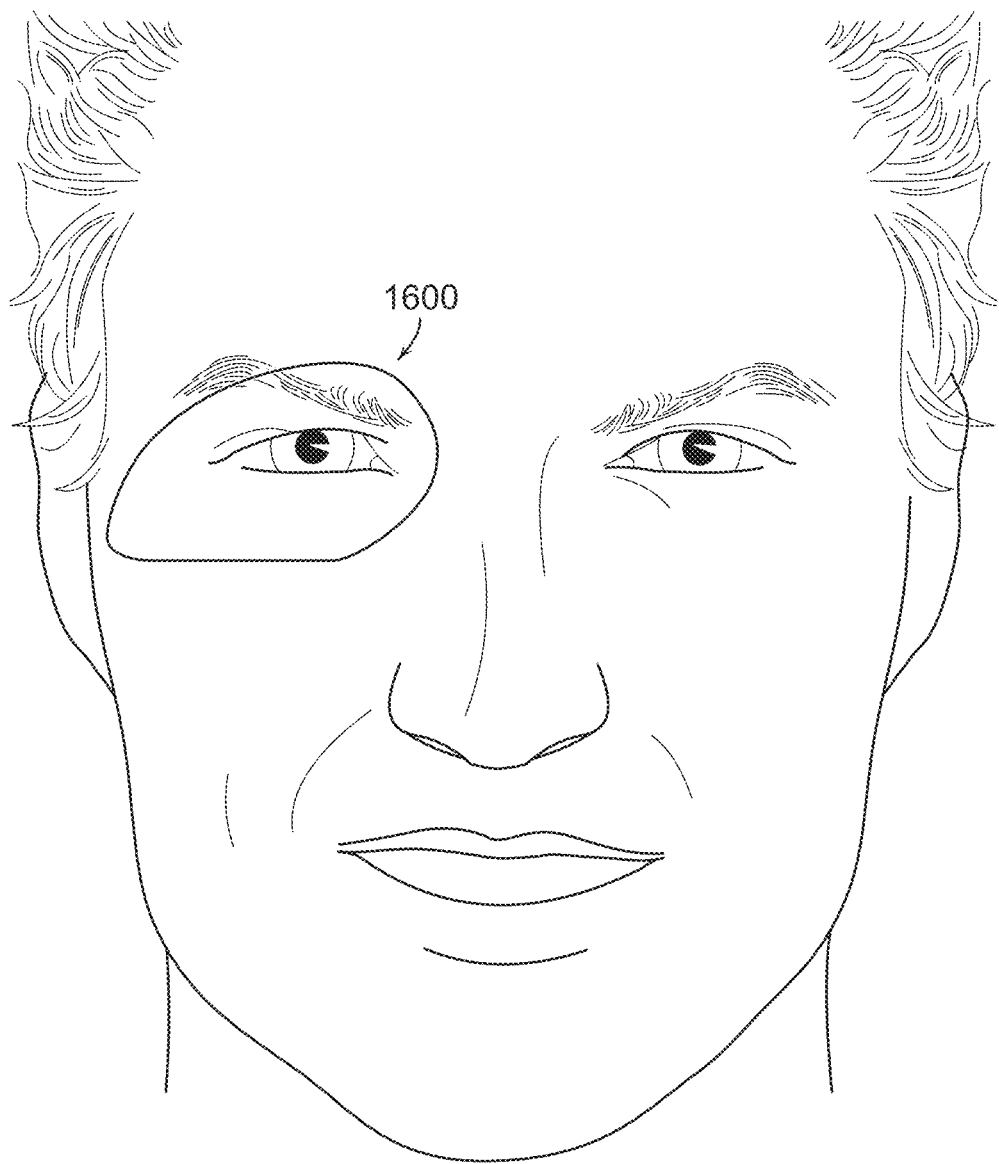
FIG. 16 illustrates an embodiment of a lens design on a male face.
Figure 17:
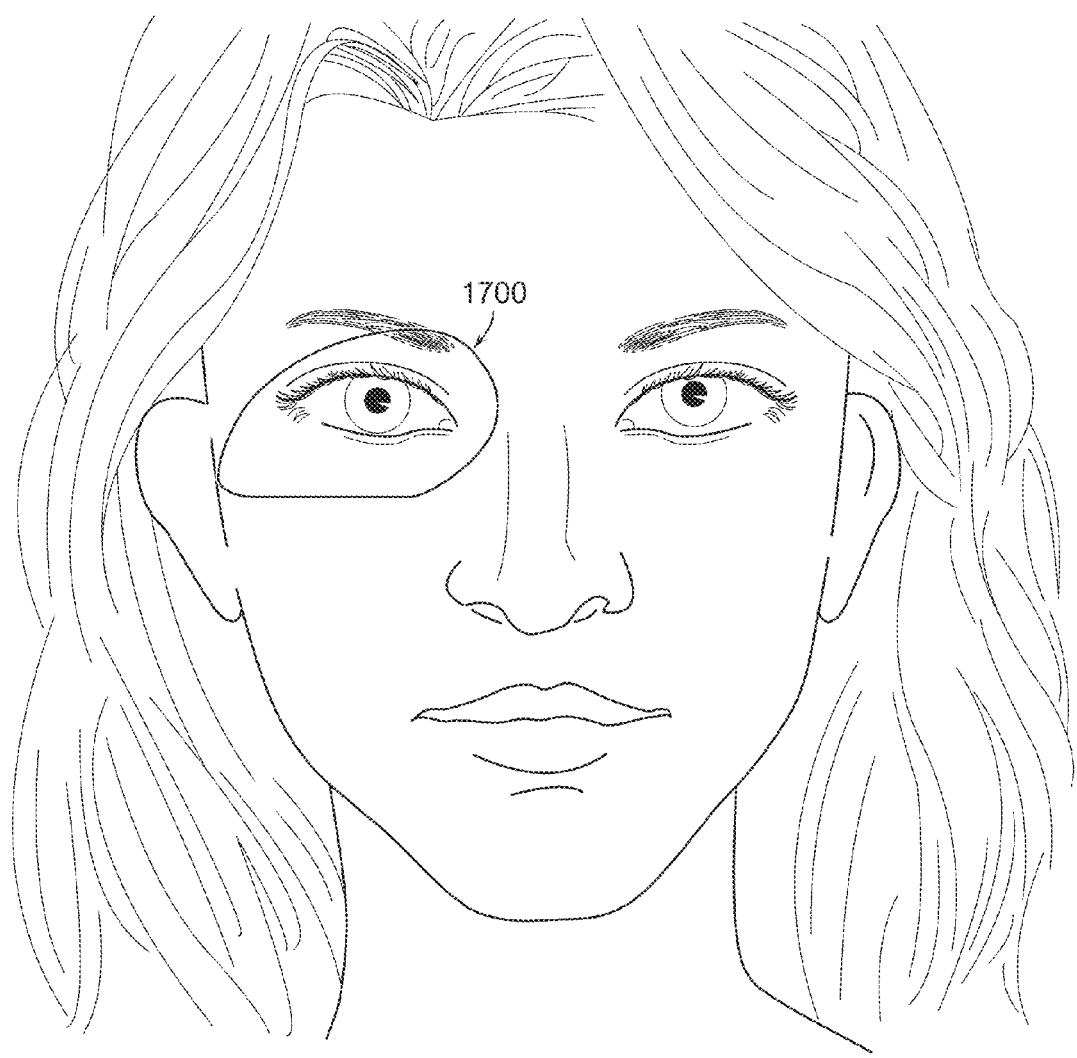
FIG. 17 illustrates an embodiment of a lens design on a female face.

FIG. 16 and FIG. 17 illustrate how the lens is situated on a human face as viewed from the front. FIG. 16 illustrates an embodiment of a lens shape design perimeter 1500 on a male face. FIG. 17 illustrates an embodiment of a lens shape design perimeter 1600 on a female face. The frame of the laser protective eyewear is used to fix the lens in place on the users head, over the eye or eyes.

Figure 18A:
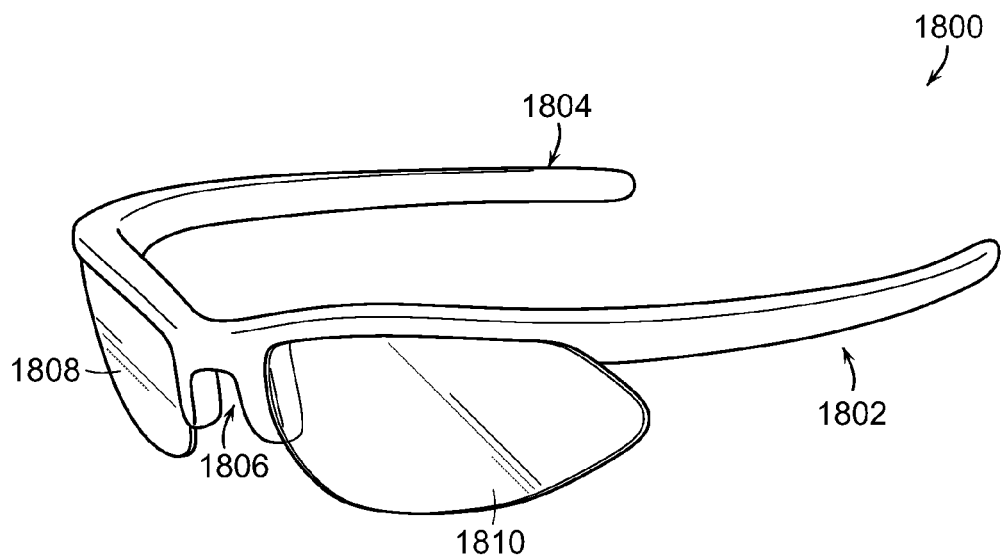
FIG. 18A illustrates an embodiment of a frame for laser protection eyewear.
Figure 18B:
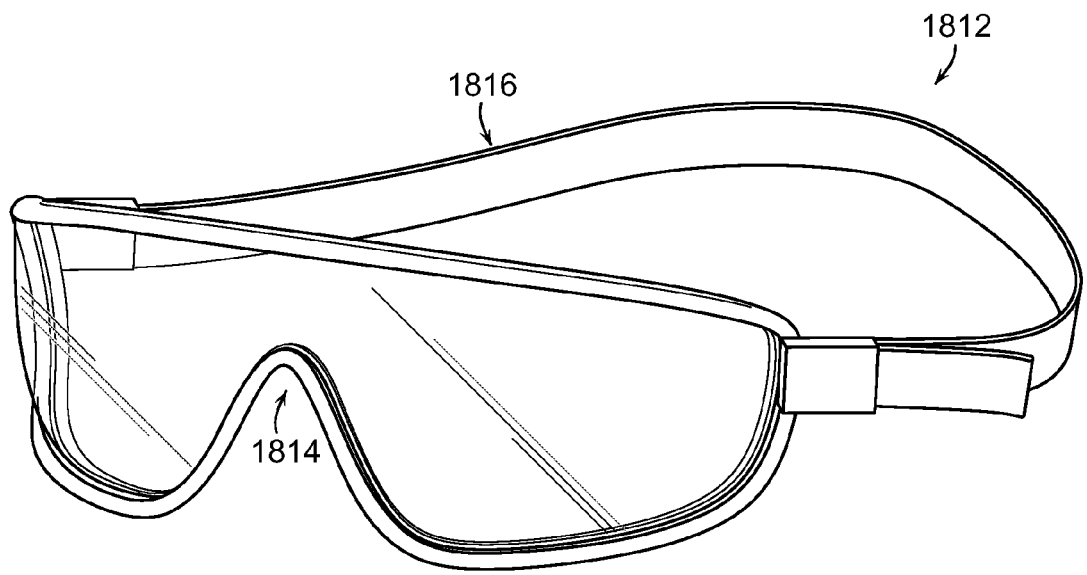
FIG. 18B illustrates an embodiment of an over-glasses goggle for laser protection eyewear according to the present teaching.

FIG. 18A and FIG. 18B illustrate two embodiments of eyewear frames according to the present teaching. FIG. 18A illustrates a frame 1800 that holds the top of the lenses 1808, 1810 with arms 1802, 1804 that curve around the face and along the contour of the curvature of the lenses. The eyewear frame provides support at the bridge of the nose 1806 and, together with the arms 1802, 1804, holds the lenses in place. In other embodiments, the lenses may be held for use over existing eyewear, such as a pair of prescription glasses. FIG. 18B illustrates an embodiment of an over-glasses goggle 1812 for laser protection eyewear according to the present teaching. The frame of the goggle provides an area at the bridge of the nose 1814 that, together with the strap 1816, holds the eyewear in place.

The coatings used in interference filters generally have precise deposited material chemical compositions, film quality, smoothness, and thickness uniformity. A variety of known evaporative and energetic deposition techniques can be used. Precision coatings are commonly applied to a number of different substrate materials, including a variety of glass, quartz, and plastic materials. Coatings for the laser protection eyewear according to the present teaching can utilize these known techniques. In addition, coatings for the laser protection eyewear can utilize known methods of substrate preparation, refractive index control, layer uniformity, and thickness monitoring in order to ensure a quality coating that achieves the unique target spectral profile. While precision coatings are also routinely applied to a variety of substrate shapes, including complex lens shapes, providing a uniform coating to complex shapes can require special substrate mounting and evaporative material shielding. In addition, precision coating also may require rotating, translating, or otherwise moving the lenses. Even small variations in film thickness and/or refractive index can result in a significant degradation of filter performance, and can lead to serious eye injuries.

Figure 19:
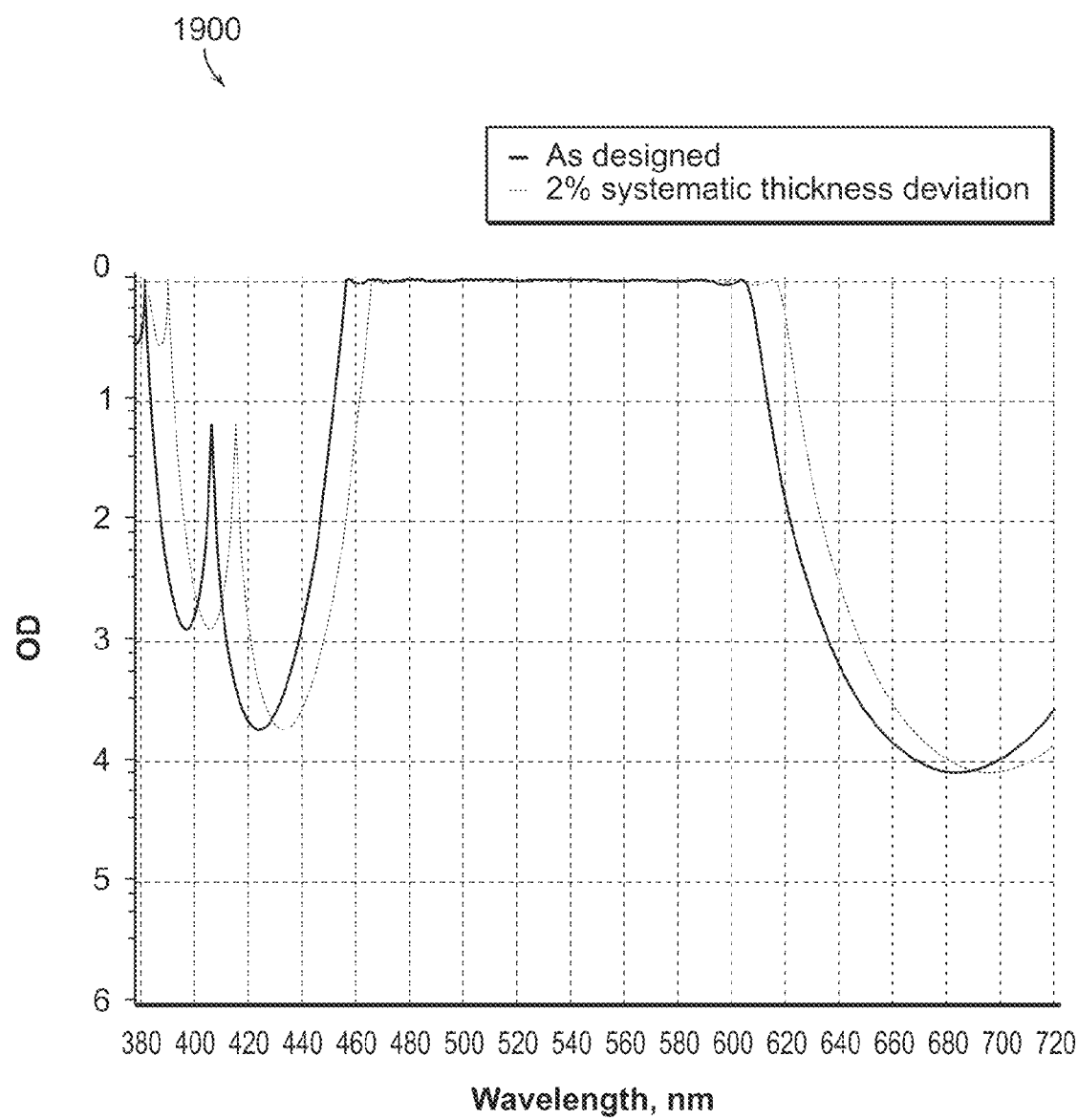
FIG. 19 illustrates the spectral distribution for 2% systematic thickness deviation.
Figure 20:
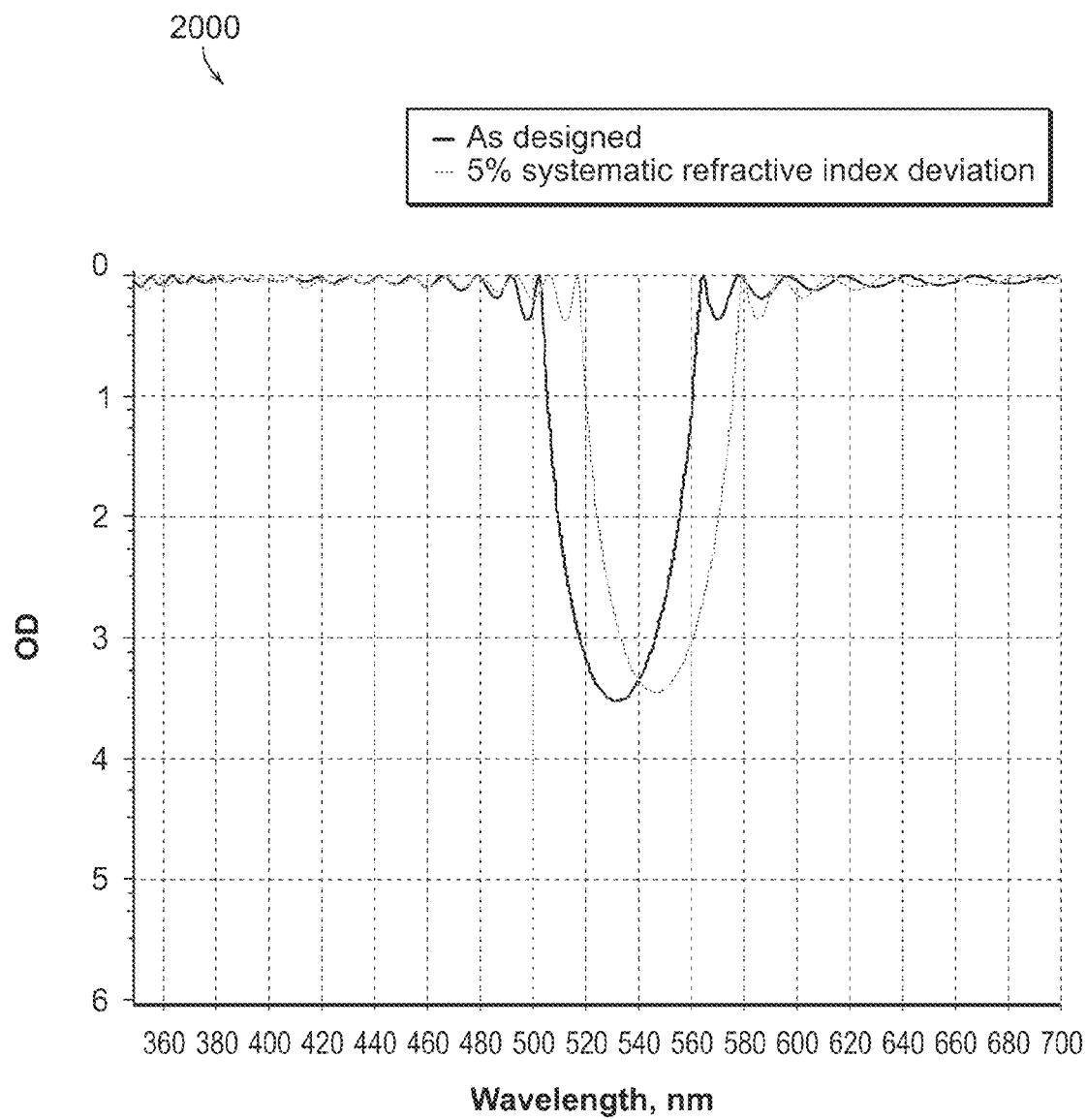
FIG. 20 illustrates the spectral distribution for 5% systematic refractive index deviation.

FIG. 19 illustrates the degradation in spectral filter profile 1900 when the layer thickness varies by more than 2%. This amount of variation will be unacceptable for some embodiments of the laser protection eyewear. FIG. 20 illustrates the degradation in spectral filter profile 1900 when the layer refractive index varies by more than 5%. FIGS. 19 and 20 illustrate systematic deviations of refractive index and physical layer thickness. Deviations in individual layer thicknesses cause ripple in the absorption profile, and shifting of the spectral features generally impacts the spectral distribution for the laser protection eyewear application less than the systematic deviation. The amount of variation shown in FIGS. 19 and 20 will be unacceptable for some embodiments. However, other embodiments can tolerate much greater thin film layer thickness uniformity and refractive index uniformity.

Inhomogeneity in the thin film layer's optical thicknesses causes spectral feature shift as a function of wavelength, as well as additional spectral ripple. For some embodiments of the laser protection eyewear of the present teaching, inhomogeneity in the thin film layer's optical thickness of more than 10%, extended over substantially the full dimension of the lens, will provide undesirable filter performance. Therefore, it is desirable for many laser protection applications to maintain thin film layer inhomogeneity of <10% across the lens. However, some embodiments of the laser protection eyewear can tolerate much greater thin film layer inhomogeneity.

In some embodiments, it is desirable that laser protection eyewear of the present teaching also provide the user with common eyewear protection features, such as scratch resistance, UVA/UVB blocking, shatter resistance, anti-static, polarizers, glare reduction, anti-reflection, sun protection for daytime wear, and darkness contrast enhancement for night time wear. In some embodiments of the present teaching, the multilayer interference filter provides these features.

Figure 21:
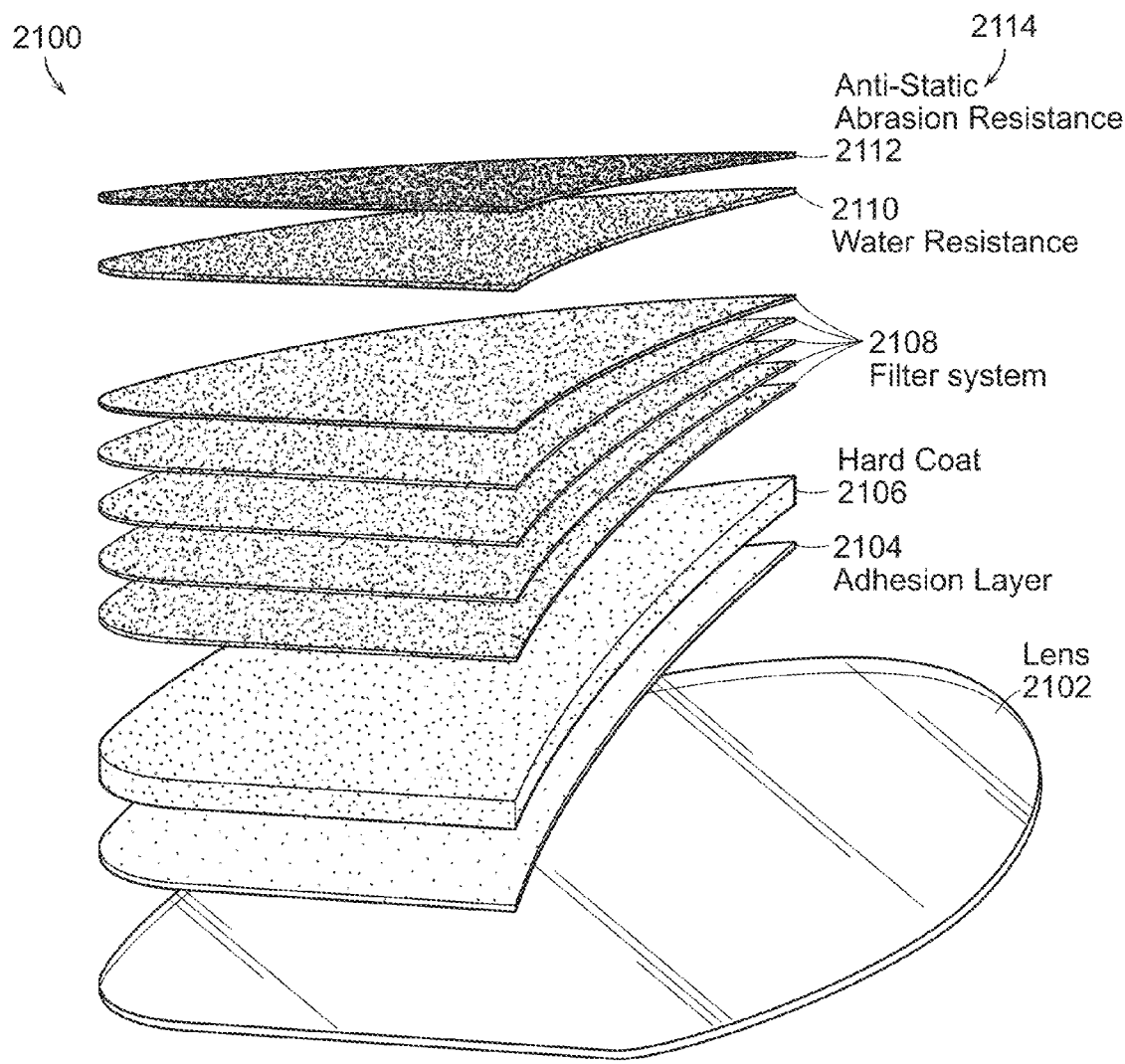
FIG. 21 illustrates an embodiment of a multi-element coating structure.

FIG. 21 illustrates an embodiment of a coating structure 2100 that can be used to provide these desirable features for practical laser protection eyewear that is designed for long term and every day use. See e.g., Eigenmann, "New developments in ophthalmic coatings on plastic lenses," (1998). An adhesion layer 2104 is used over the lens, 2102, which may be polycarbonate, PMMA, glass, or other material, in order to improve the adhesion and uniformity of the multilayer coating, particularly for plastic or other inorganic lens substrate types. Chromium, chromium oxide, silicon, or other materials may be used in different embodiments. Next, a hardcoat layer 2106 is provided, for example a glassy material like silicon dioxide, which improves the shatter resistance of the lens.

FIG. 21 also illustrates the multilayer interference coating 2108, which provides the spectral filtering appropriate to block the laser radiation. Water-resistant coatings 2110, as well as anti-static 2114 and abrasion resistant 2112 layers, can be deposited on the multilayer interference coating. In various embodiments, the coatings can be applied in different orders. For some embodiments, it is desirable to have the same or different coatings applied to both sides of the lens. For example, effects of thin film distortion can be mitigated by applying coatings on both sides of the lens. In addition, in some embodiments, coatings are also deposited on the edges of the lens. The interference filter design is sensitive to the optical properties of the materials that surround it. As such, the anticipated total layer structure, both between the lens substrate and the multilayer filter structure, and over the multilayer thin film profiles, should be known and included in the interference filter design to ensure that the appropriate filter response is provided.

Plastic materials are an attractive substrate for most eyeglass lenses, including laser protection eyewear, because of its high strength-to-weight ratio, mechanical flexibility, ability to mold into different shapes, mechanical resilience, shatter resistance, and low cost. Ophthalmic lenses are made from several different types of plastic materials, such as CR39, PMMA, and polycarbonates, which have refractive indexes from 1.5-1.65. However, plastic materials can be difficult to coat because of their large coefficient of thermal expansion, low thermal stability, water absorption, and low surface energy that reduces thin film adhesion. Plastics also develop higher surface electric charge that attracts dust and dirt. Thus, plastic lenses, such as polycarbonate, PMMA and CR39, will need an additional coating layer or layers to improve adhesion, reduce stress, increase hardness, and increase abrasion resistance. Improving adhesion can be accomplished by using wet chemical treatment, exposure to flame, UV radiation, plasma cleaning/etching, or chemical catalysis.

There are numerous other factors that need to be considered in the lens design, such as selecting materials and layer designs that have high transparency in the visible region. Also, high and low refractive index values should be chosen that reduce the number of layers, and that are also suitable for evaporative or energetic thin film deposition processes. Materials should also have low toxicity and low solubility in air, water, and other manufacturing chemicals. Generally, thicker layers are able to provide more spectral features with steeper absorption edges as a function of wavelength, and reduced oscillation in transparent regions. However, manufacturing high quality thick coating of multiple thin film layers is known to be challenging.

In one specific embodiment, a combination of $Ta_2O_5$ as a high index material, and $SiO_2$ as a low index material, is used to provide a quality multilayer film in the range of 2-5 microns thick on various plastic substrates. Other embodiments of the laser protection eyewear interference filter will use other known thin film materials, such as SiO, $Al_2O_3$, $HfO_2$, $ZrO_2$, $TiO_2$, $Nb_2O_5$, $Si_3N_4$, ZnO, and others. See e.g., Friz "Coating materials," (2003).

Figure 22:
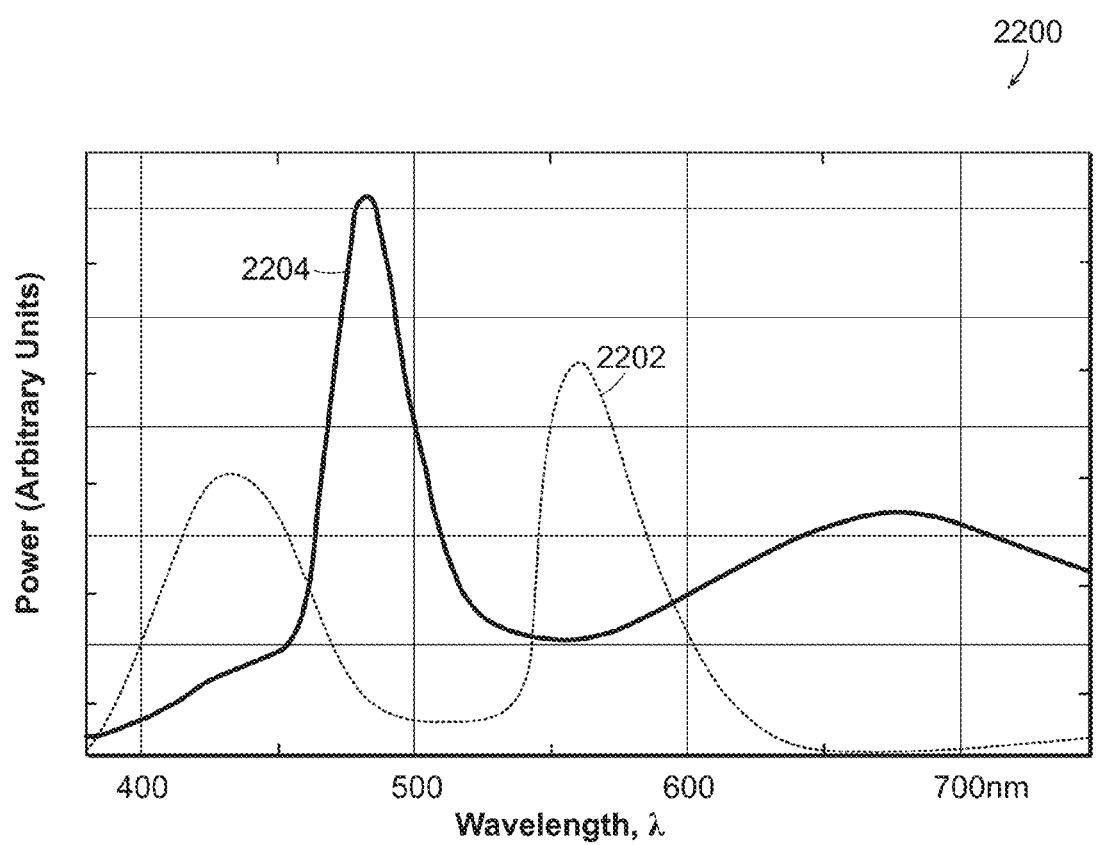
FIG. 22 illustrates the spectral distribution of metameric stimuli.

Another aspect of the present teaching is to provide laser protection eyewear with good color balance that does not impair the user's color vision. Metamers are spectral distributions, which, when viewed by a human observer, produce the same color. Color matching, which necessarily involves the perception of a viewer, is covered by a branch of color science called colorimetry, and is governed by experimentally obtained results of the human perception of color as a function of the spectral distribution of observed stimuli. Colorimetry is governed by a series of standards and procedures called the CIE Colorimetric System. See e.g., Wyszecki, "Color Science Concepts and Methods," (2000). Quantitatively, two spectral distributions are metamers when their spectral radiant power distributions, $P_{1\lambda} d\lambda$ and $P_{2\lambda} d\lambda$, satisfy the following equations:

$$\int_\lambda P_{1\lambda} \bar{r}(\lambda) d\lambda = \int_\lambda P_{2\lambda} \bar{r}(\lambda) d\lambda.$$

$$\int_\lambda P_{1\lambda} \bar{g}(\lambda) d\lambda = \int_\lambda P_{2\lambda} \bar{g}(\lambda) d\lambda.$$

$$\int_\lambda P_{1\lambda} \bar{b}(\lambda) d\lambda = \int P_{2\lambda} \bar{b}(\lambda) d\lambda.$$

where $\bar{r}(\lambda)$, $\bar{g}(\lambda)$, and $\bar{b}(\lambda)$ are the spectral tristimulus values of a monochromatic stimulus with unit radiant power, with respect to three fixed primary stimuli, $\lambda_r = 700$ nm, $\lambda_g = 546.1$ nm, and $\lambda_b = 435.8$ nm. FIG. 22 illustrates a spectral distribution of two metamers 2200. Note that a spectral distribution with a peak in the violet and a peak in the yellow region of the spectrum 2202 exhibits the same color to an observer as a spectral distribution with a peak in the blue-green and a peak in the red region of the spectrum 2204.

Thus, one aspect of the present teaching is to use colorimetry for laser protection eyewear to add colorization and/or color balance to the spectral distributions provided by the multilayer filters to compensate for filtering parts of the spectrum, and to generally enhance the user's visual experience. Using the mathematics of color science, spectral profiles are established that provide a particular colorization and/or color balance for the user. The multilayer thin film profile is determined by the rendering process described herein. Furthermore, in some embodiments, colorization and/or color balance is used to improve visibility and/or contrast. In other embodiments, colorization and/or color balance is used to highlight or enhance a particular color (e.g. safety or warning indicators or navigational lights). In other embodiments, colorization is used to aid in stimulation or alertness or generate a sense of calm or well being. In still other embodiments, colorization enhances night vision. In yet other embodiments, colorization enhances contrast in low-illumination, and/or high-illumination environments.

The color perceived by a user through the filter depends on both the color of the object and also on the spectral properties of the illumination source. For example, in an aircraft cockpit, the flight deck instruments are all backlit or illuminated. See e.g., Cockpit Lighting, A330 Flight Crew Manual. There is generally flood lighting in the instrument panel. Panel lighting brightness is adjustable. Work surfaces and other consoles are serviced by spot lights and flood lights. Individual reading lights are typical for captain and copilot. Some type of overhead lighting, such as dimmable domes, provides for general cockpit illumination. White lighting is typically either incandescent, fluorescent, or LED type. Colored lighting is of a filtered white light or LED lighting. Some embodiments of the present teaching utilize a target filter spectral distribution, using a particular color objective together with the spectral distribution, for cockpit illumination.

For pilots in takeoff and landing situations at airports with lighted runways, there are a variety of illumination systems used for navigation and safety. See e.g., Aeronautical Lighting and Other Airport Visual Aids, FAA publication AIM0201. For example, approach light systems are a configuration of signal lights starting at the landing threshold and extending into the approach area for a distance of between 1400-3000 feet, depending on the runway type. These include red, white, and blue lights. Visual Approach Slope Indicator (VASI) systems utilize either white, white and red, or tricolor (red green and amber lights), which may be continuous or flashing. Runway end identifier lights are white flashing lights. Runway edge light systems are usually white, but may also be yellow. Lights marking the end of a runway may emit red light toward the runway and green light outward from the runway. Runway centerline lights are white. Touchdown zone lights are white. Taxiway centerline lead-off and lead-on lights are color coded green and yellow. Land and hold-short lights are white. Runway status light system uses primarily red, but also include white lights.

Older airports will typically be illuminated using bright white incandescent lights with color filters to achieve colored lights. However, it is a trend to use LED lighting for runway illumination because such light systems are more energy efficient and can have high brightness. Thus, some embodiments of the laser protection eyewear according to the present teaching will include spectral filter profiles that not only provide the desired protection from laser radiation threats, but that also provide clear visualization and color perception for blue, white, green, yellow and red lighting emitted from incandescent light sources with color filter and/or LED devices. To this end, some embodiments of the laser protection eyewear of the present teaching utilize a filter spectral distribution that has a particular color objective together with the spectral distribution for airport illumination, and also preserve or enhance the visibility of navigation and safety lighting.

Figure 23A:
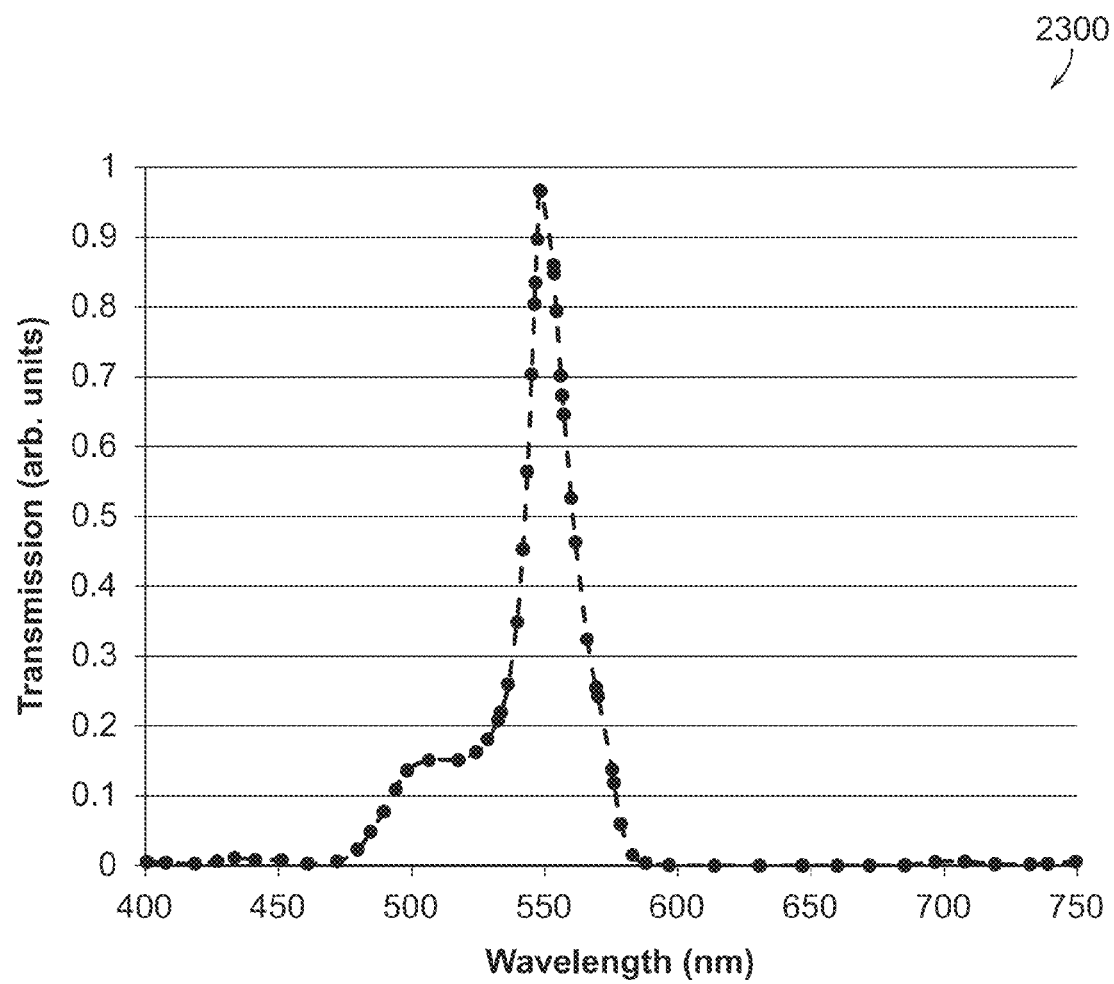
FIG. 23A illustrates a green color spectrum of an LCD device.
Figure 23B:
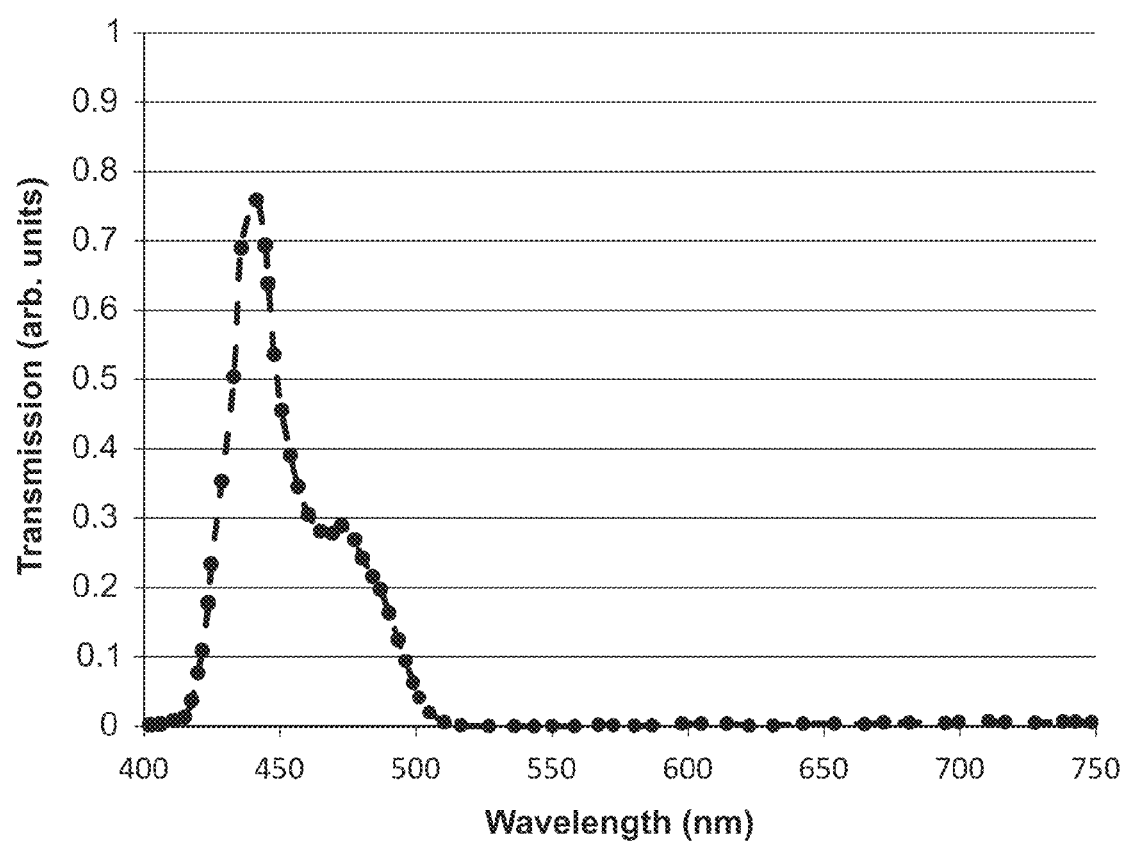
FIG. 23B illustrates a blue color spectrum of an LCD device.
Figure 23C:
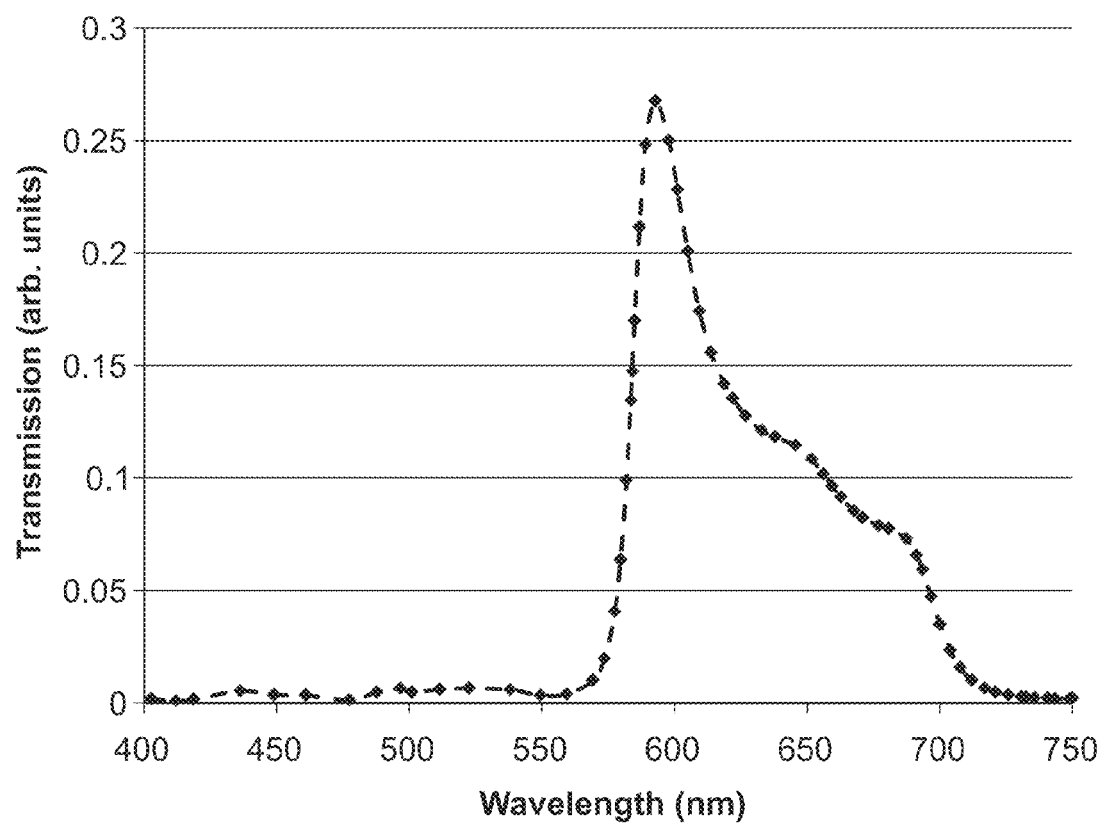
FIG. 23C illustrates a red color spectrum of an LCD device.
Figure 23D:
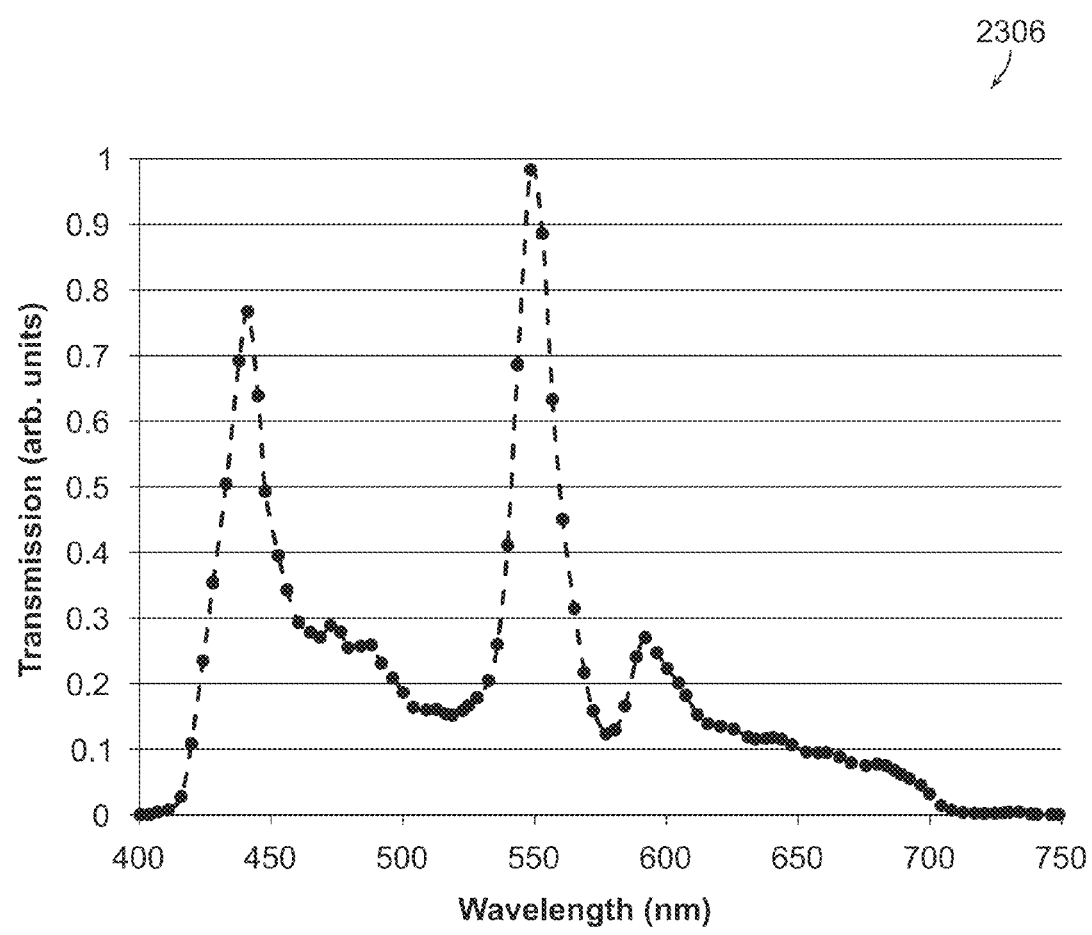
FIG. 23D illustrates a white color spectrum of an LCD device.

Another aspect of the laser protection eyewear of the present teaching is to provide suitable color balance and good color contrast for viewing of common cockpit instrumentation and lighting. In a typical cockpit, this means suitable color balance for an LCD, or like screen. LCD screens are commonly used for cockpit instruments, laptops, tablets, cell phone, and smartphone. FIGS. 23A-23D illustrate the spectral distributions of an LCD display device. See e.g., Seime "Colorimetric characterization of LCD and DLP projection displays," (2003). The distribution includes contributions from three filters used to generate green, red, and blue spectral illumination. The three primary colors are modulated in various amounts by the LCD device to provide a spectral illumination distribution that provides perceived color to an observer. The modulation occurs on a pixel-by-pixel basis, thus providing a two-dimensional color display for substantially arbitrary scenes. FIG. 23A illustrates the color spectrum caused by the green filter in the LCD device, with broad spectral emission from 490 nm-580 nm, and a peak around 550 nm. FIG. 23B illustrates the color spectrum caused by the blue filter in the LCD device, with broad spectral emission from 420 nm-490 nm, and a peak around 445 nm. FIG. 23C illustrates the color spectrum caused by the red filter in the LCD device, with broad spectral emission from 580 nm-700 nm, and a peak around 590 nm. FIG. 23D illustrates the color spectrum of a white modulation condition in the LCD device, which includes spectral components from light through red, green, and blue filters.

Figure 24A:
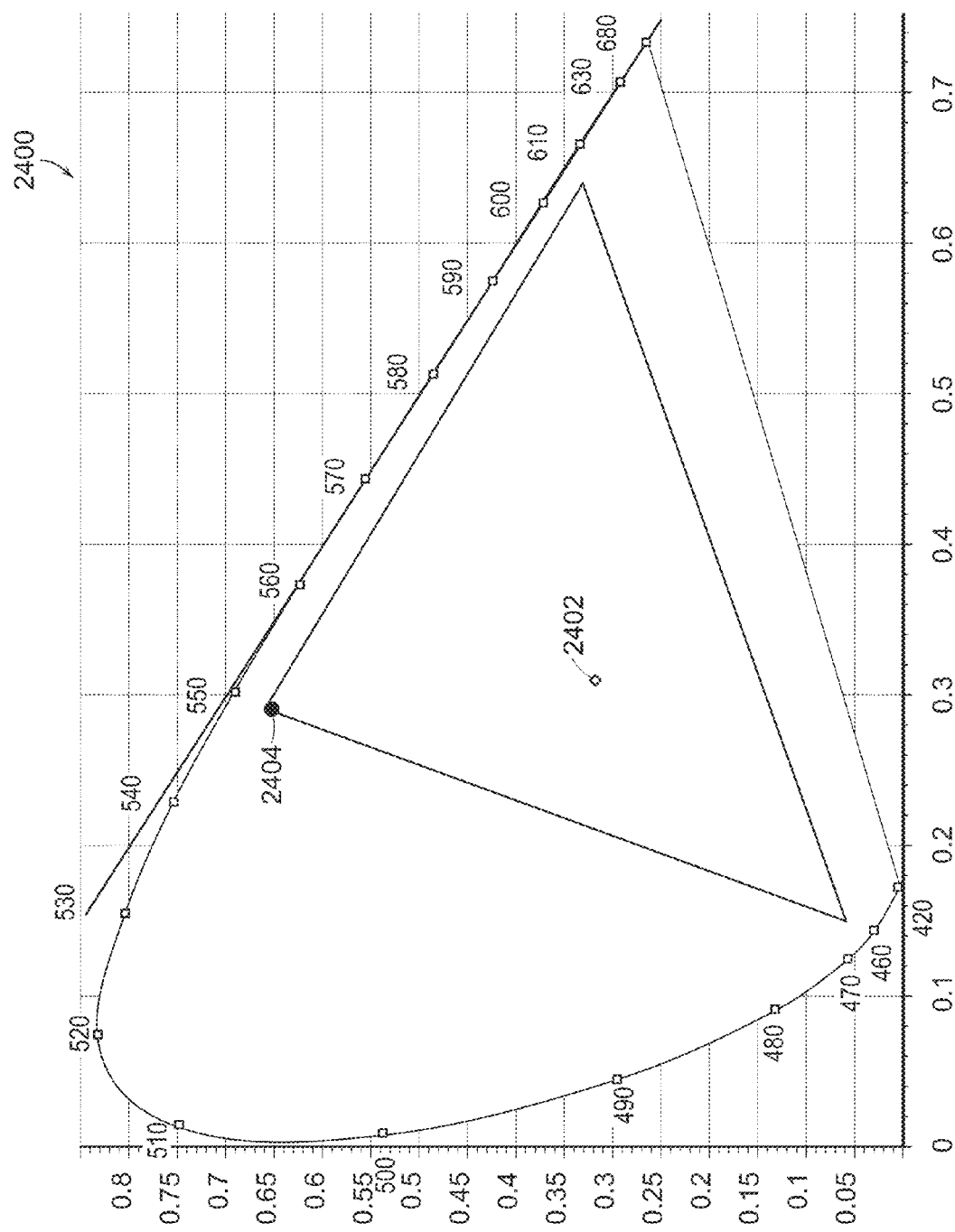
FIG. 24A illustrates the chromaticity coordinate for a green LCD spectrum.
Figure 24B:
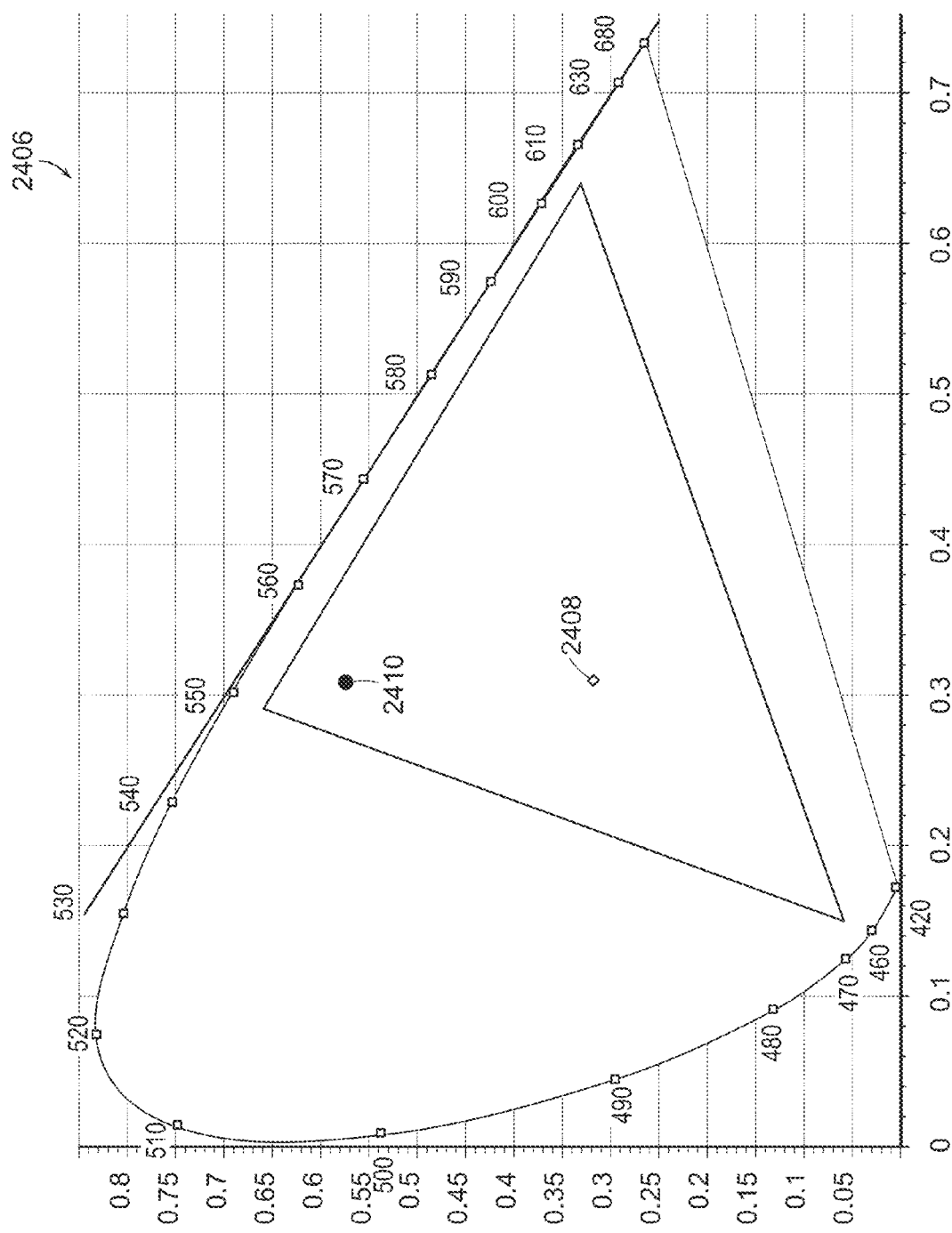
FIG. 24B illustrates the chromaticity coordinate for a filtered green LCD spectrum.

The spectral distributions emanating from the LCD displays of FIG. 23, as viewed with and without filtering from the notch-plus-two-edge filter 300 (FIG. 3), can be converted into chromaticity coordinates of the CIE 1964 colorimetric system. FIG. 24A illustrates the chromaticity coordinate 2404 plotted on the (x,y)-chromaticity diagram 2400 for the green LCD spectrum. FIG. 24B illustrates the chromaticity coordinate 2410 plotted on the (x,y)-chromaticity diagram 2406 for the green LCD spectrum and filtered through the notch-plus-two-edge filter 300. The perceived color of the filtered version remains in the green region of the chromaticity diagram.

Figure 25A:
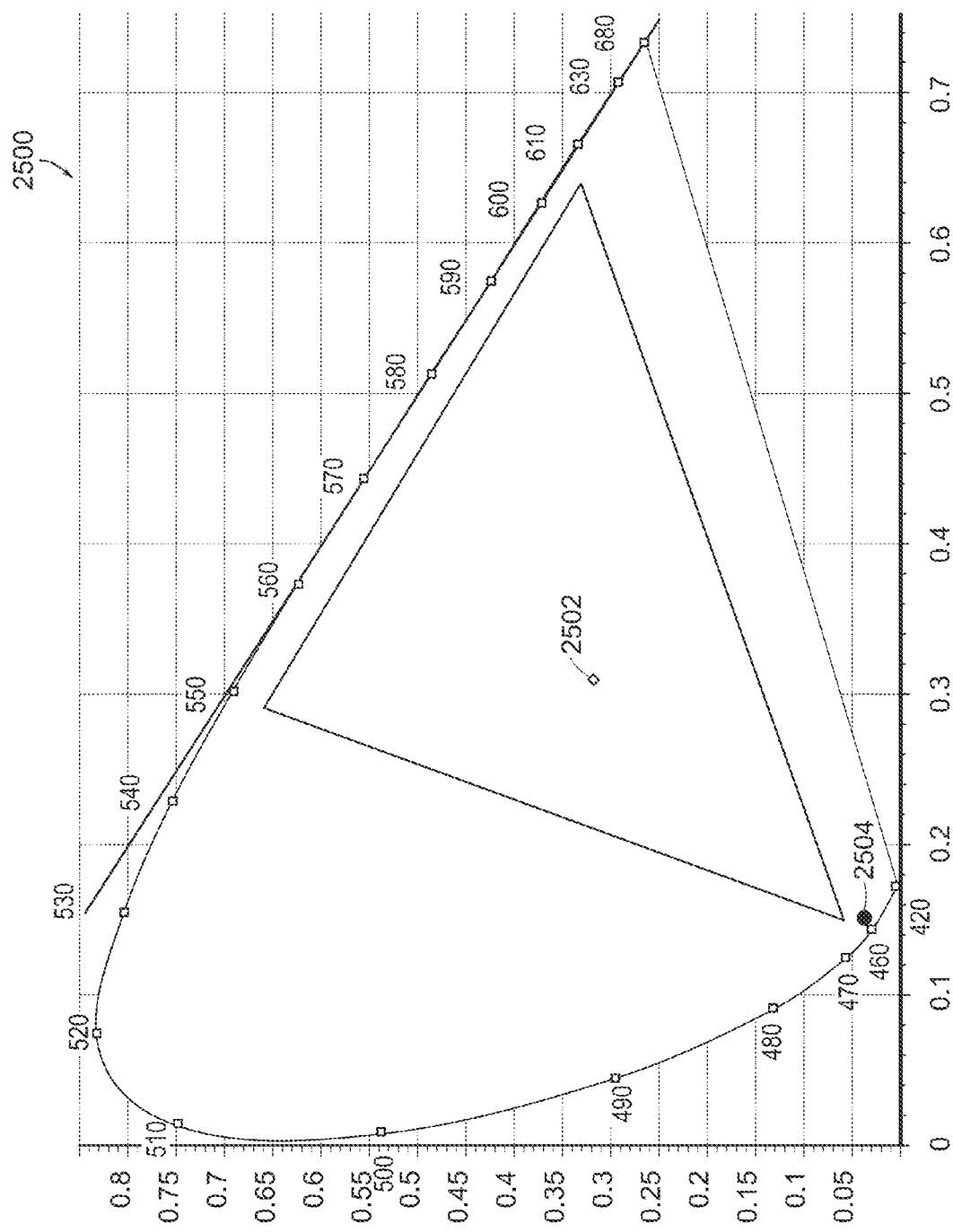
FIG. 25A illustrates the chromaticity coordinate for a blue LCD spectrum.
Figure 25B:
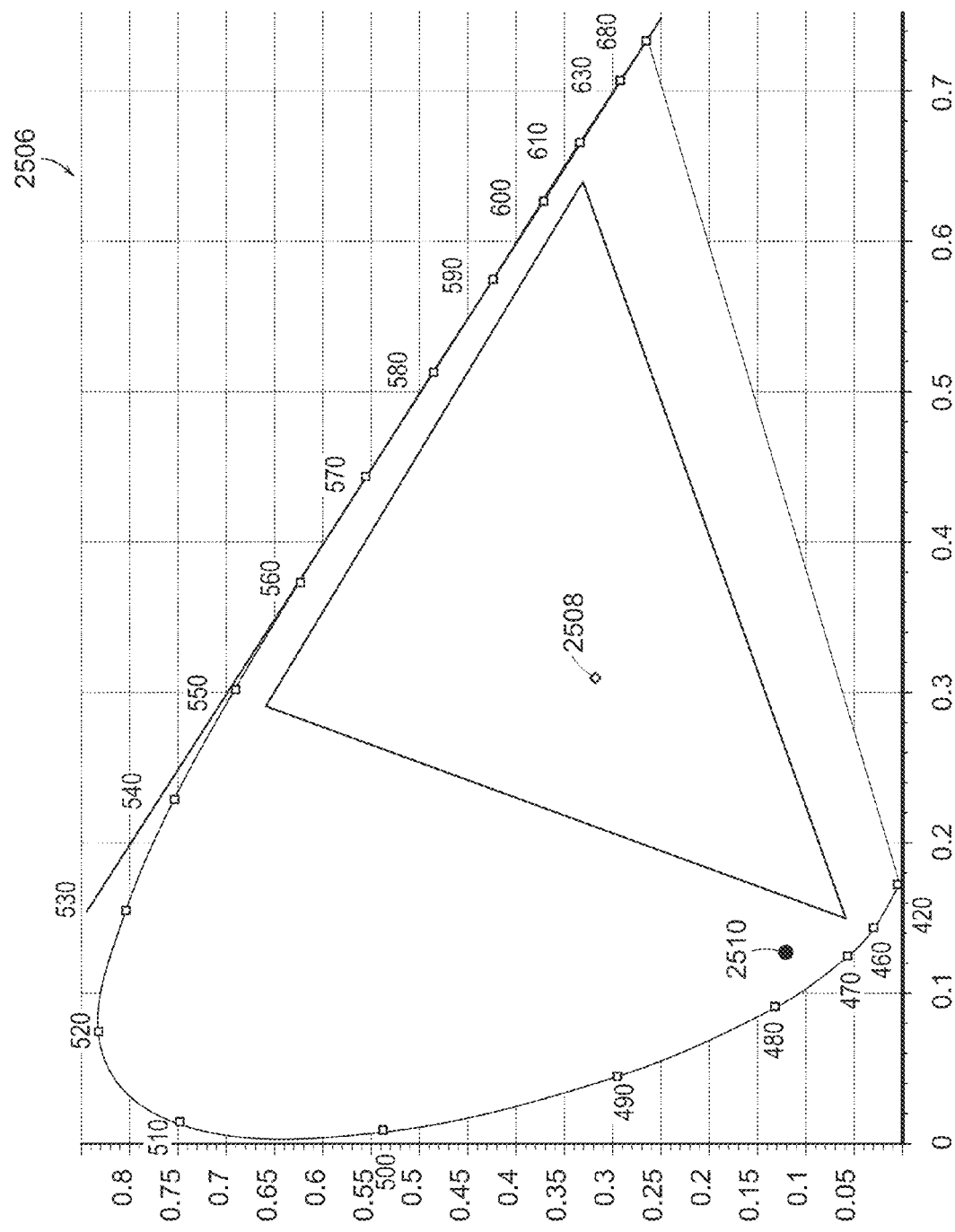
FIG. 25B illustrates the chromaticity coordinate for a filtered blue LCD spectrum.

FIG. 25A illustrates the chromaticity coordinate 2504 plotted on the (x,y)-chromaticity diagram 2500 for the blue LCD spectrum. FIG. 25B illustrates the chromaticity coordinate 2510 plotted on the (x,y)-chromaticity diagram 2506 for the blue LCD spectrum and filtered through the notch-plus-two-edge filter 300. The perceived color of the filtered version remains in the blue region of the chromaticity diagram.

Figure 26B:
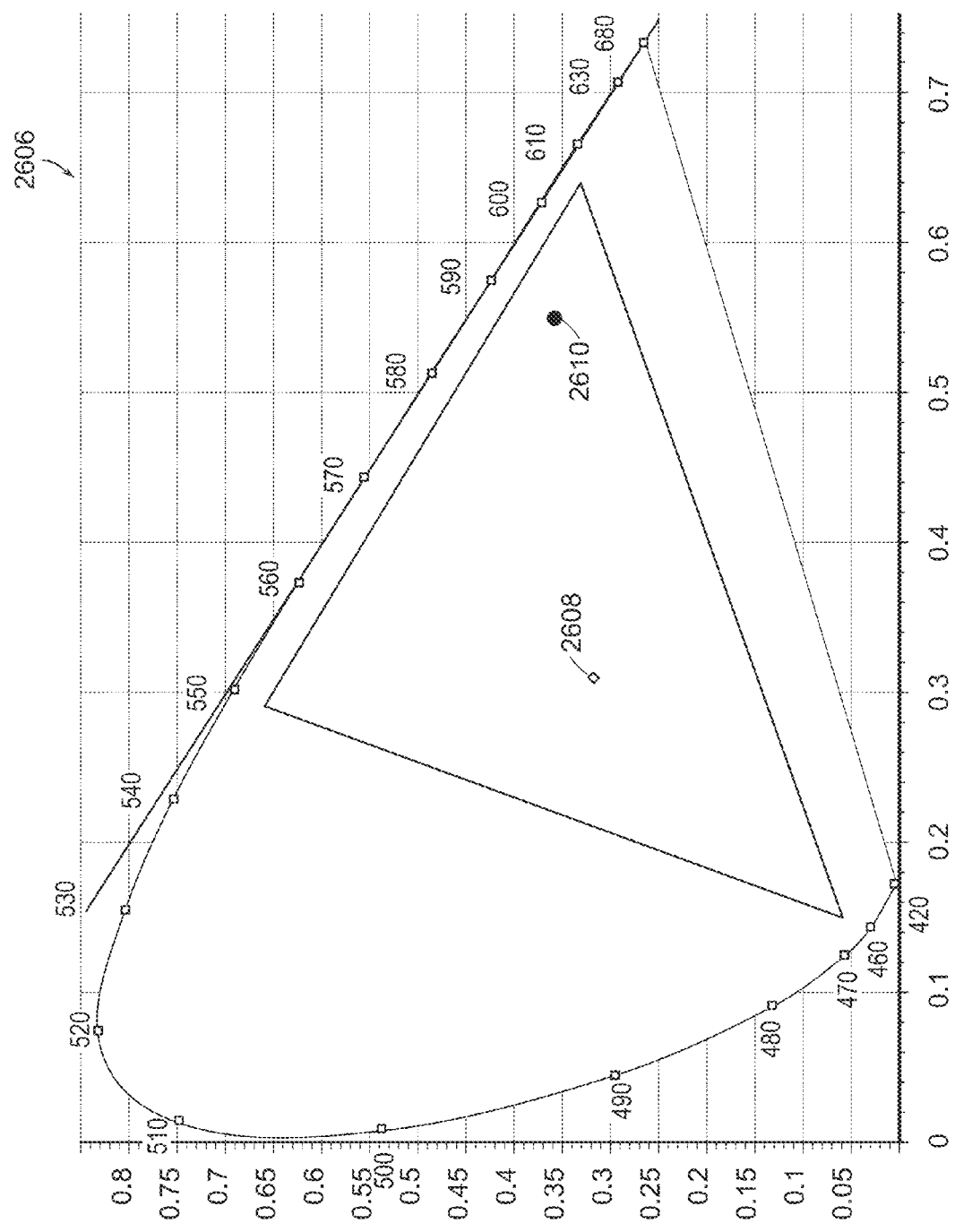
FIG. 26B illustrates the chromaticity coordinate for a filtered red LCD spectrum.

FIG. 26A illustrates the chromaticity coordinate 2604 plotted on the (x,y)-chromaticity diagram 2600 for the red LCD spectrum. FIG. 26B illustrates the chromaticity coordinate 2610 plotted on the (x,y)-chromaticity diagram 2606 for the red LCD spectrum and filtered through the notch-plus-two-edge filter 300. The perceived color of the filtered version remains in the red region of the chromaticity diagram.

Figure 27A:
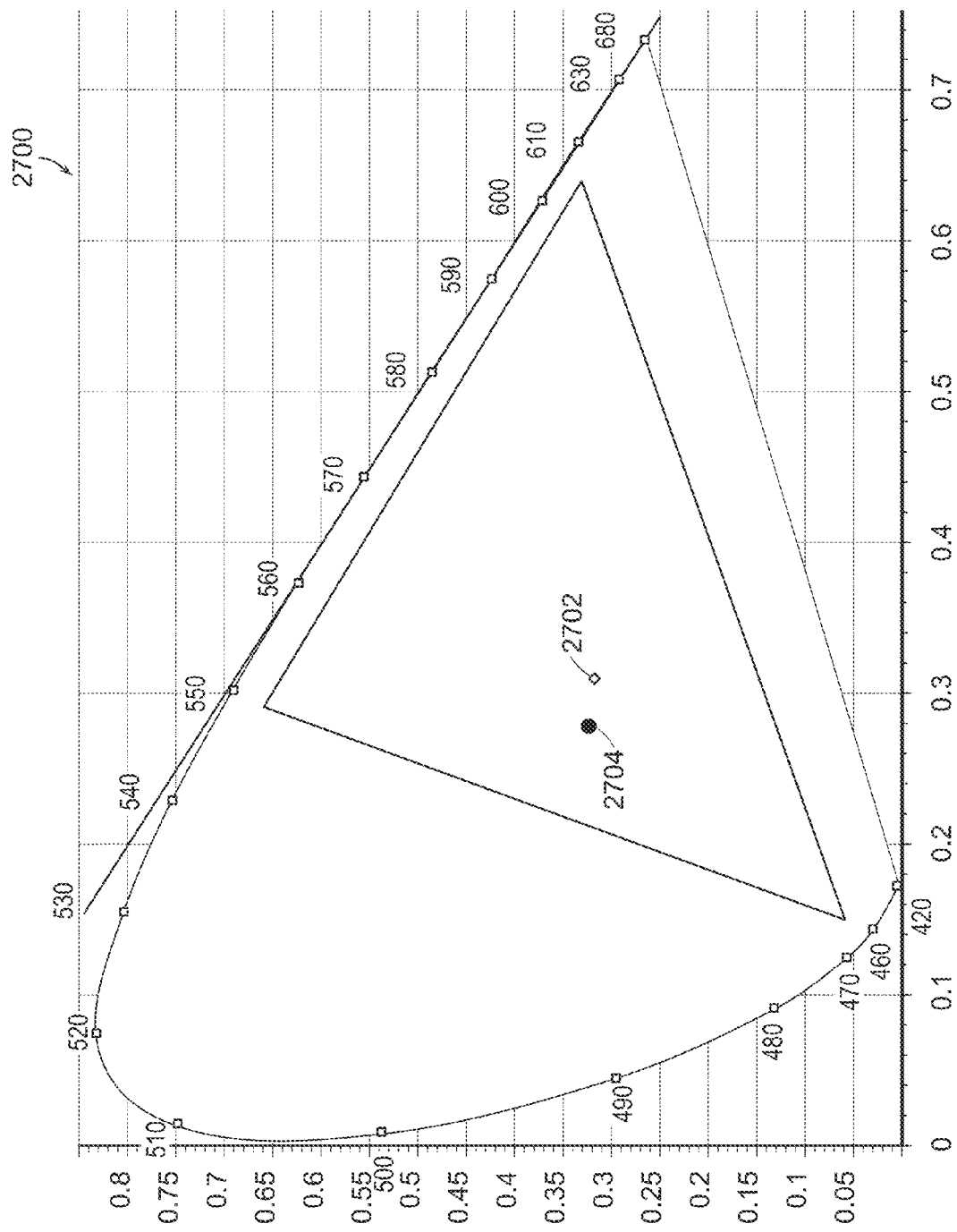
FIG. 27A illustrates the chromaticity coordinate for a white LCD spectrum.
Figure 27B:
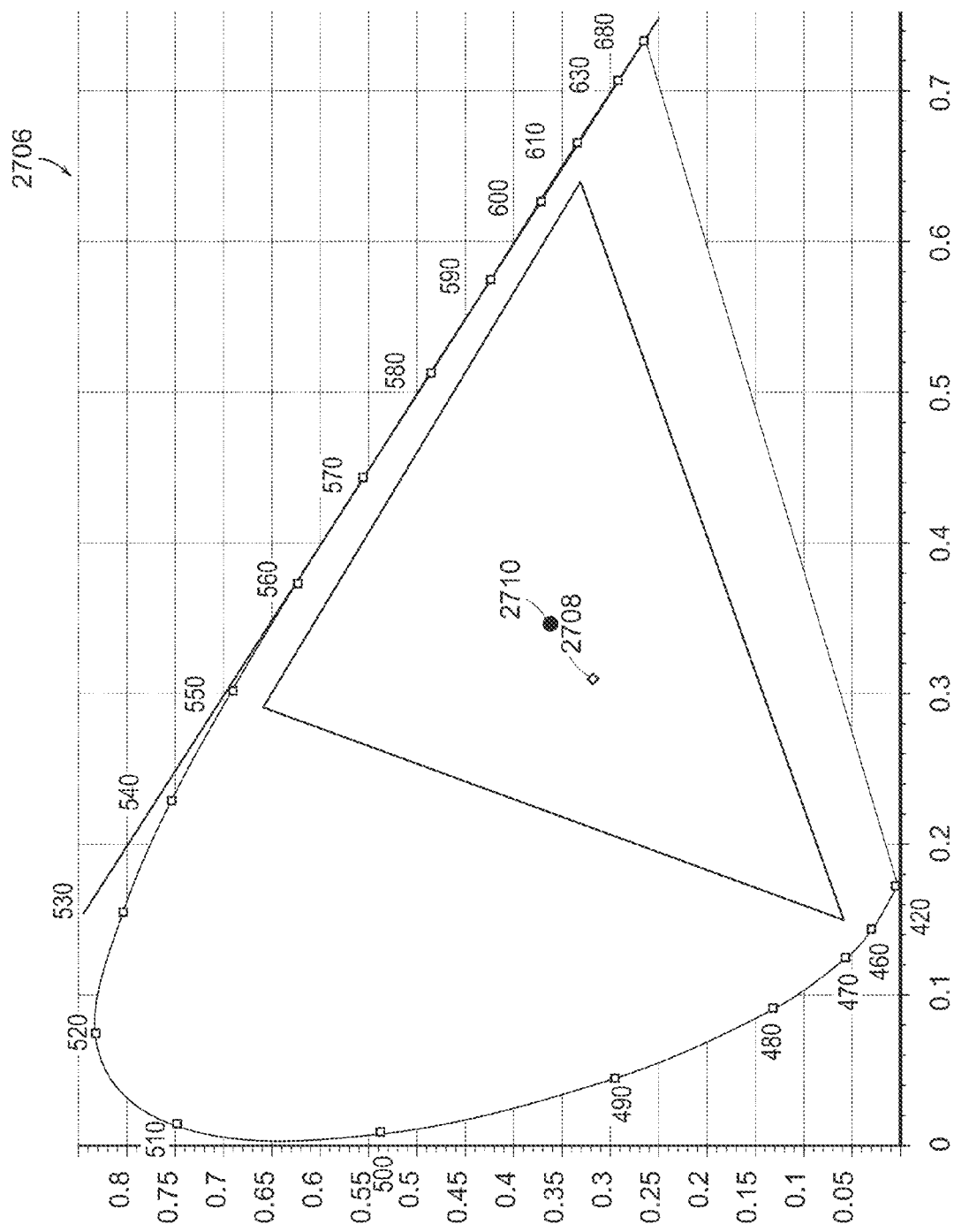
FIG. 27B illustrates the chromaticity coordinate for a filtered white LCD spectrum.

FIG. 27A illustrates the chromaticity coordinate 2704 plotted on the (x,y)-chromaticity diagram 2700 for the white LCD spectrum. The perceived color is close to the uniform chromaticity point, slightly towards the blue region of the chromaticity diagram. FIG. 27B illustrates the chromaticity coordinate 2710 plotted on the (x,y)-chromaticity diagram 2706 for the white LCD spectrum and filtered through the notch-plus-two-edge filter 300. The perceived color is close to the uniform chromaticity point, slightly toward the yellow/amber region of the chromaticity diagram. These effects of the filtering on the perceived colors emanating from a luminous LCD display are desirable for maintaining color balance and contrast from the instrumentation in a cockpit environment. FIG. 28 illustrates a table listing the chromaticity coordinates from the previous examples (FIGS. 24-27).

The colorimetric system is provided as an internationally standard computational basis for the prediction of the perceived color of a color stimulus. In 1976, the CIE provided a standard that was intended to be more suitable for describing color difference known as the CIE 1976 (L*,u*,v*)-space and color difference formula. This basis provides a three-dimensional color space that is considered more uniform than the two-dimensional color chromaticity points, and thus provides a better basis for measuring color difference between two color stimuli. The color difference is calculated from the L*,u*,v*coordinates as: $\Delta E = \{(\Delta L^*)^2 + (\Delta u^*)^2 + (\Delta v^*)^2\}^{1/2}$.

FIG. 29 illustrates Table 5, which lists the L*,u*,v* coordinates and color difference for each of the green, blue, red, and white LCD as both unfiltered and filtered through the notch-plus-two-edge filter. All color differences between the filtered and unfiltered LCD spectral stimuli are less than 64. FIG. 29 also illustrates Table 6, which lists the color difference between the white LCD as both unfiltered and filtered through the spectral profile of a green notch filter of the prior art, 200 (FIG. 2). The white LCD filtered through the green notch filter 200 has a larger color difference (109.4) compared to the notch-plus-two-edge filter 300 (FIG. 3) with the color difference of 63.5. Large color difference implies color distortion to the observer of the color stimuli. Thus, it is an object of the present teaching to provide a laser protection filter spectral profile that provides a color difference of not more than 70. These embodiments of the color properties of the laser protection eyewear, are examples only, and do not limit the teaching of this disclosure. Other filter designs, color objectives, and color differences would be utilized to achieve different color perception objectives in different embodiments, as would be obvious to those knowledgeable in the state of the art.

Another aspect of the laser protection eyewear of the present teaching is to provide color balance suitable to support viewing of head-up display technology in airplane cockpits and other transportation equipment. See e.g., Hou "Ultra-bright heads-up displays using a method of projected color images by combination of LEDs and polymer-dispersed liquid crystals," (2014). It is known to those familiar with the state of the art that head-up display devices use illumination elements that may be single color, which is typically green, with similar spectrum to the spectrum shown in FIG. 23A. The illumination elements for head-up display devices may also be multicolor and exhibit color spectra similar to those shown in FIGS. 23A-23D.

Another aspect of the laser protection eyewear of the present teaching is to provide color balance suitable for military applications. Modern military aircraft cockpits are outfitted with blue-spectrum lighting to better accommodate night vision goggles. Therefore, in some embodiments, the laser protection eyewear of the present teaching includes a transmission region that passes blue lighting, and can also include additional spectral bands that provide a particular metameric objective.

EQUIVALENTS

While the applicant's teaching is described in conjunction with various embodiments, it is not intended that the applicants' teaching be limited to such embodiments. On the contrary, the applicant's teaching encompass various alternatives, modifications, and equivalents, as will be appreciated by those of skill in the art, which may be made therein without departing from the spirit and scope of the teaching.

What is claimed is:

1. A laser protection lens comprising:
   a) an optically transparent material having a perimeter shape that follows a contour of a user's eye socket ridge, a horizontal shape, and a vertical shape, wherein the horizontal shape comprises at least two different angles with respect to a normal of the plane of the user's face defined by a line oriented parallel to a line connecting the center of both eyes that passes though the glabella and by a line connecting the glabella to the subnasale; and
   b) a multilayer interference coating applied to at least one of an inside and an outside surface of the optically transparent material, the multilayer interference coating having a spectral filter profile with at least 20 dB reduction of optical transmission for at least one of 445 nm, 532 nm, and 610 nm wavelength light propagating at angles within forty-five degrees with respect to the normal of the plane of the user's face.

2. The laser protection lens of claim 1 wherein the multilayer interference coating is formed on both the inside and the outside surface of the optically transparent material.

3. The laser protection lens of claim 2 wherein a thickness of the multilayer interference coating on at least one of the inside and outside surfaces is chosen to reduce at least one of compressive and tensile forces.

4. The laser protection lens of claim 1 wherein the vertical shape is substantially flat.

5. The laser protection lens of claim 1 wherein the optically transparent material is selected from the group consisting of glass, quartz, plastic, polycarbonate, PMMA and CR39.

6. The laser protection lens of claim 1 wherein the optically transparent material has optical transmission greater than 50% over a portion of the visible spectrum.

7. The laser protection lens of claim 1 wherein an offset angle with respect to the normal of the plane of the user's face of the lens is between zero and twenty degrees.

8. The laser protection lens of claim 1 wherein the vertical shape is curved.

9. The laser protection lens of claim 1 wherein the vertical shape has at least two different angles with respect to the normal of the plane of the user's face.

10. The laser protection lens of claim 1 wherein a total thickness of the multilayer interference coating is less than or equal to 5 microns.

11. The laser protection lens of claim 1 wherein a 3 dB bandwidth around the 445 nm, 532 nm, and 610 nm wavelengths is less than 30 nm.

12. The laser protection lens of claim 1 further comprising at least one additional coating applied to at least one of the inside and the outside surface of the optically transparent material, the at least one additional coating is selected from the group consisting of scratch resistance, UVA/UVB blocking, shatter resistance, anti-static, polarizing, glare reduction, anti-reflection, sun protection, and darkness contrast enhancement.

13. The laser protection lens of claim 1 wherein the lens comprises a prescription lens.

14. The laser protection lens of claim 1 wherein the spectral filter profile of the multilayer interference coating enhances a user's color perception of illuminated displays.

15. The laser protection lens of claim 14 wherein the illuminated displays are selected from a group consisting of instrumentation displays, LCD displays, plasma displays, cell phone/smartphone displays, tablet displays, computer displays, and laptop displays.

16. The laser protection lens of claim 1 wherein the spectral filter profile of the multilayer interference coating enhances a user's viewability of a head-up display.

17. The laser protection lens of claim 1 wherein the spectral filter profile of the multilayer interference coating enhances a user's night vision.

18. The laser protection lens of claim 1 wherein the spectral filter profile of the multilayer interference coating is chosen to provide a color difference ΔE defined by the CIE 1976 (L*,u*,v*) color difference formula of less than 100 when viewing illuminated displays.

19. The laser protection lens of claim 1 wherein the spectral filter profile of the multilayer interference coating is chosen to provide a color difference ΔE defined by the CIE 1976 (L*,u*,v*) color difference formula of less than 50 viewing illuminated displays.

20. The laser protection lens of claim 1 wherein the spectral filter profile comprises a color difference ΔE of less than 100 between an unfiltered white LCD spectrum and the unfiltered white LCD spectrum filtered through the spectral filter profile.

21. A laser protection lens comprising:
a) an optically transparent material having a perimeter shape that follows a contour of a user's eye socket ridge; and
b) a first multilayer interference coating applied to an inside surface of the optically transparent material and a second multilayer interference coating applied to an outside surface of the optically transparent material, the first and second multilayer interference coating together having a spectral filter profile with at least 20 dB reduction of optical transmission for at least one of 445 nm, 532 nm, and 610 nm wavelength light, and a color difference ΔE defined by the CIE 1976 (L*,u*,v*) color difference formula, of less than 100 between an unfiltered white LCD spectrum and the unfiltered white LCD spectrum filtered through the spectral filter profile.

22. The laser protection lens of claim 21 wherein the optically transparent material is selected from the group consisting of glass, quartz, plastic, polycarbonate, PMMA and CR39.

23. The laser protection lens of claim 21 wherein the optically transparent material has optical transmission greater than 50% over a portion of the visible spectrum.

24. The laser protection lens of claim 21 wherein a total thickness of the multilayer interference coating is less than or equal to 5 microns.

25. The laser protection lens of claim 21 further comprising at least one additional coating applied to at least one of the inside and the outside surface of the optically transparent material, the additional coating selected from the group consisting of scratch resistance, UVA/UVB blocking, shatter resistance, anti-static, polarizing, glare reduction, anti-reflection, sun protection, and darkness contrast enhancement.

26. The laser protection lens of claim 21 wherein the lens comprises a prescription lens.

27. The laser protection lens of claim 21 wherein the spectral filter profile of the multilayer interference coating enhances a user's color perception of illuminated displays.

28. The laser protection lens of claim 27 wherein the illuminated displays are selected from a group consisting of cockpit instrumentation displays, LCD displays, plasma displays, cell phone/smartphone displays, tablet displays, computer displays, and laptop displays.

29. The laser protection lens of claim 21 wherein the color difference ΔE is less than 50.

30. The laser protection lens of claim 21 wherein the spectral filter profile of the multilayer interference coating enhances a user's viewability of a head-up display.

31. The laser protection lens of claim 21 wherein the spectral filter profile of the multilayer interference coating enhances a user's night vision.

32. Laser protection eyewear comprising:
a) a frame that supports at pair of laser protection lenses in a substantially fixed position with respect to a plane of a user's face defined by a line oriented parallel to a line connecting the center of both eyes that passes though the glabella and by a line connecting the glabella to the subnasale, each of the pair of laser protection lenses comprising an optically transparent material having a perimeter shape that follows a contour of a user's eye socket ridge, a horizontal shape, and a vertical shape; and
b) a multilayer interference coating applied to at least one of an inside and outside surface of the optically transparent material, the multilayer interference coating having a spectral filter profile with at least 10 dB reduction of optical transmission for at least one of 445 nm, 532 nm, and 610 nm wavelength light propagating at angles within forty-five degrees with respect to the normal of the plane of the user's face and having at least 10 dB optical reduction over a wavelength band from at least one of 445 nm to the ultraviolet region and 610 nm the infrared region.

33. The laser protection eyewear of claim 32 wherein at least one lens of the pair of laser protection lens comprises a prescription lens.

34. The laser protection eyewear of claim 32 wherein the frame supports an over-glasses configuration.

35. The laser protection eyewear of claim 32 wherein the spectral filter profile comprises a color difference ΔE of less than 100 between an unfiltered white LCD spectrum and the unfiltered white LCD spectrum filtered through the spectral filter profile.

* * * * *